United States Patent
Tufaro et al.

(10) Patent No.: US 11,110,137 B2
(45) Date of Patent: *Sep. 7, 2021

(54) COMBINATION THERAPY FOR TREATMENT OF BRAIN CANCERS

(71) Applicant: DNATRIX, INC., Houston, TX (US)

(72) Inventors: Frank Tufaro, Rancho Santa Fe, CA (US); Joanna J. Peterkin, Rancho Santa Fe, CA (US)

(73) Assignee: DNATRIX, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/997,552

(22) Filed: Aug. 19, 2020

(65) Prior Publication Data

US 2020/0376050 A1 Dec. 3, 2020

Related U.S. Application Data

(63) Continuation of application No. 16/346,310, filed as application No. PCT/US2017/059611 on Nov. 1, 2017.

(60) Provisional application No. 62/416,075, filed on Nov. 1, 2016.

(51) Int. Cl.

| A61K 35/761 | (2015.01) |
| A61P 35/00 | (2006.01) |
| A61K 39/395 | (2006.01) |
| A61K 9/00 | (2006.01) |
| C07K 16/28 | (2006.01) |
| A61K 45/06 | (2006.01) |
| A61K 39/00 | (2006.01) |

(52) U.S. Cl.
CPC .......... *A61K 35/761* (2013.01); *A61K 9/0019* (2013.01); *A61K 9/0085* (2013.01); *A61K 39/3955* (2013.01); *A61K 45/06* (2013.01); *A61P 35/00* (2018.01); *C07K 16/2818* (2013.01); *A61K 2039/505* (2013.01); *A61K 2039/54* (2013.01); *A61K 2039/545* (2013.01); *C07K 2317/24* (2013.01); *C12N 2710/10321* (2013.01)

(58) Field of Classification Search
CPC ...... A61K 35/761; A61K 35/17; A61K 38/19; C12N 15/861; C07K 2317/76; C07K 16/2827

See application file for complete search history.

(56) References Cited

U.S. PATENT DOCUMENTS

| 8,974,777 | B2 | 3/2015 | Cascallo Piqueras |
| 9,061,055 | B2 | 6/2015 | Fueyo |
| 10,238,698 | B2 | 3/2019 | Tufaro |
| 2016/0143967 | A1 | 5/2016 | Fueyo-Margareto et al. |

FOREIGN PATENT DOCUMENTS

| EP | 3293201 | 3/2018 |
| WO | WO 2010/072900 | 7/2010 |
| WO | WO 2015/127501 | 9/2015 |
| WO | WO 2016/008976 | 1/2016 |
| WO | WO 2017/205875 | 11/2017 |

OTHER PUBLICATIONS

ClinicalTrials.gov published by NIH US National Library of Medicine, which is first published on Feb. 15, 2011, pp. 1-26.*
"History of Changes for Study: NCT02798406", dated Sep. 30, 2016, retrieved from: clinicaltrials.gov/ct2/history/NCT02798406?V_6=View#StudyPageTop on Mar. 19, 2020.
Battaglia, Gina. "Immunotherapy Combinations Offer Hope in Glioblastoma.", dated Oct. 8, 2015, retrieved from: www.uclahealth.org/neurosurgery/Workfiles/Site-Neurosurgery/News/Immunotherpy-Cornbinations-Offer-Hope-in-Glioblastoma.pdf on Mar. 19, 2020.
Choi, Audrey H., et al. "From benchtop to bedside: a review of oncolytic virotherapy." *Biomedicines* 4.3 (2016): 18.
Extended European Search Report issued in European Application No. 17868307.4, dated Apr. 24, 2020.
Jiang, Hong, et al. "Oncolytic adenovirus: preclinical and clinical studies in patients with human malignant gliomas." *Current Gene Therapy* 9.5 (2009): 422-427.
International Search Report and Written Opinion dated Jan. 25, 2018, for Application No. PCT/US2017/059611.
Fueyo, Juan, et al. "A mutant oncolytic adenovirus targeting the Rb pathway produces anti-glioma effect in vivo." *Oncogene* 19.1 (2000): 2-12.
Fueyo, Juan, et al. "Preclinical characterization of the antiglioma activity of a tropism-enhanced adenovirus targeted to the retinoblastoma pathway." *Journal of the National Cancer Institute* 95.9 (2003): 652-660.
Martínez-Vélez, Naiara, et al. "The oncolytic virus Delta-24-RGD elicits an antitumor effect in pediatric glioma and DIPG mouse models." *Nature communications* 10.1 (2019): 1-10.

* cited by examiner

Primary Examiner — Bao Q Li
(74) Attorney, Agent, or Firm — Parker Highlander PLLC

(57) ABSTRACT

Methods of treating a subject having a brain tumor comprising (a) administering an oncolytic virus and (b) administering a therapeutic antibody to said subject.

31 Claims, 7 Drawing Sheets

| Drug | Dose | Dose Frequency | Route of Administration | Regimen |
|---|---|---|---|---|
| DNX-2401 Dose escalation (3 Cohorts) | 5e8 vp 5e9 vp 5e10 vp | Single dose | Intratumoral Injection | Day 0 |
| DNX-2401 Declared Dose | TBD | Single dose | Intratumoral Injection | Day 0 |
| Pembrolizumab | 200 mg | Each dose given every three weeks | Intravenous infusion over 30 minutes | Initial dose – Day 7 Every 3 weeks (First day of each cycle) |

FIG. 2

|  | Clinically Stable | | Clinically Unstable | |
| --- | --- | --- | --- | --- |
|  | Tumor Imaging | Treatment | Tumor Imaging | Treatment |
| 1st radiologic evidence of PD | Repeat imaging at ≥ 4 weeks at site to confirm PD | May continue study treatment at the investigator's discretion while awaiting confirmatory imaging results | Repeat tumor imaging at ≥ 4 weeks to confirm PD per physician discretion only | Discontinue treatment |
| Repeat tumor imaging confirms PD | No additional tumor imaging required | Discontinue treatment after discussion with the DNAtrix Medical Monitor or designee | No additional tumor imaging | N/A |
| Repeat tumor imaging shows SD, PR, or CR | Continue regularly scheduled tumor imaging assessments | Continue study treatment at the investigator's discretion | Continue regularly scheduled tumor assessments | May restart study treatment if condition has improved and/or clinically stable per investigator's discretion |

FIG. 4

| Hematology | Chemistry | Urinalysis | Other | Tumor Pathology |
|---|---|---|---|---|
| • White blood cell count with differential (neutrophils, absolute neutrophil count (ANC), basophils, eosinophils, lymphocytes, monocytes and other identified components, as applicable)<br>• Red blood cell count<br>• Hemoglobin<br>• Hematocrit<br>• Platelet count | • Albumin<br>• Alkaline phosphatase<br>• ALT (SGPT)<br>• AST (SGOT)<br>• BUN<br>• Calcium<br>• Carbon dioxide<br>• Chloride<br>• Creatinine<br>• Glucose, fasting<br>• Potassium<br>• Sodium<br>• Total bilirubin<br>• Direct bilirubin<br>• Total protein<br>• Uric acid<br>• HbA1c | • Appearance<br>• Color<br>• pH<br>• Specific gravity<br>• Ketones<br>• Protein<br>• Glucose<br>• Bilirubin<br>• Nitrite<br>• Urobilinogen<br>• Occult blood<br>• Leukocyte esterase<br><br>*Microscopic examination only if the results of the macroscopic evaluation are positive and indicate a microscopic exam* | Coagulation<br>• aPTT<br>• PT<br>• INR<br>Pregnancy Test<br>• Urine/Serum pregnancy test (and serum as necessary to confirm + urine result) per local practice<br>Hormone Test<br>• FSH<br>Screening Serology<br>• HIV<br>• Hepatitis, [A,B (Anti-HBc and HBsAg) and C]<br>• TB testing, if indicated<br>Thyroid Function<br>• TSH<br>• T3<br>• Free T3/Free T4 | • Histopathology<br>• Genetic testing (mutational analysis, etc.)<br>• Virus studies may be performed (e.g., PCR, IHC, etc.)<br>• Other analyses, to be determined<br><br>Tumor tissue will be archived for future analysis |

FIG. 5

| Toxicity | Hold Treatment For Grade | Timing for Restarting Treatment | Treatment Discontinuation |
|---|---|---|---|
| Diarrhea/Colitis | 2-3 | Toxicity resolves to Grade 0-1 | Toxicity does not resolve within 12 weeks of last dose or inability to reduce corticosteroid to 10 mg or less of prednisone or equivalent per day within 12 weeks |
|  | 4 | Permanently discontinue |  |
| AST, ALT, or Increased Bilirubin | 2 | Toxicity resolves to Grade 0-1 | Toxicity does not resolve within 12 weeks of last dose |
|  | 3-4 | Permanently discontinue (See exception below)[a] |  |
| Type 1 diabetes mellitus (if new onset) or Hyperglycemia | T1DM or 3-4 | Hold pembrolizumab for new onset Type 1 diabetes mellitus or Grade 3-4 hyperglycemia associated with evidence of beta cell failure | Resume pembrolizumab when patients are clinically and metabolically stable |
| Hypophysitis | 2-4 | Toxicity resolves to Grade 0-1. Therapy with pembrolizumab can be continued while endocrine replacement therapy is instituted | Toxicity does not resolve within 12 weeks of last dose or inability to reduce corticosteroid to 10 mg or less of prednisone or equivalent per day within 12 weeks |
| Hyperthyroidism | 3 | Toxicity resolves to Grade 0-1 | Toxicity does not resolve within 12 weeks of last dose or inability to reduce corticosteroid to 10 mg or less of prednisone or equivalent per day within 12 weeks |
|  | 4 | Permanently discontinue |  |

FIG. 6A

| | | | |
|---|---|---|---|
| Hypothyroidism | | Therapy with pembrolizumab can be continued while thyroid replacement therapy is instituted | Therapy with pembrolizumab can be continued while thyroid replacement therapy is instituted |
| Infusion Reaction | 2[b] | Toxicity resolves to Grade 0-1 | Permanently discontinue if toxicity develops despite adequate premedication |
| | 3-4 | Permanently discontinue | Permanently discontinue |
| Pneumonitis | 2 | Toxicity resolves to Grade 0-1 | Toxicity does not resolve within 12 weeks of last dose or inability to reduce corticosteroid to 10 mg or less of prednisone or equivalent per day within 12 weeks |
| | 3-4 | Permanently discontinue | Permanently discontinue |
| Renal Failure or Nephritis | 2 | Toxicity resolves to Grade 0-1 | Toxicity does not resolve within 12 weeks of last dose or inability to reduce corticosteroid to 10 mg or less of prednisone or equivalent per day within 12 weeks |
| | 3-4 | Permanently discontinue | Permanently discontinue |
| All Other Drug-Related Toxicity[c] | 3 or Severe | Toxicity resolves to Grade 0-1 | Toxicity does not resolve within 12 weeks of last dose or inability to reduce corticosteroid to 10 mg or less of prednisone or equivalent per day within 12 weeks |
| | 4 | Permanently discontinue | Permanently discontinue |

*FIG. 6B*

COMBINATION THERAPY FOR TREATMENT OF BRAIN CANCERS

CROSS-REFERENCE TO RELATED APPLICATION

This application is a continuation of U.S. application Ser. No. 16/346,310, filed Apr. 30, 2019, as a national phase application under 35 U.S.C. § 371 of International Application No. PCT/US2017/059611, filed Nov. 1, 2017, which claims the benefit under 35 U.S.C. § 119(e) of U.S. Provisional Patent Application No. 62/416,075 filed Nov. 1, 2016, which applications are incorporated herein by reference in their entireties for all purposes.

BACKGROUND

Field of the Invention

The present application is directed to the fields of medicine, oncology, viral therapy and immune therapy. In particular, it is directed to the use, in combination, of an oncolytic adenovirus and an antibody directed to PD-1, in the treatment of brain cancers, such as glioblastomas and gliosarcomas.

Description of the Related Art

Cancers are a large family of diseases characterized by the uncontrolled growth of cells in a body. It is one of the leading causes of death, with an estimated 14.1 million new cases worldwide per year (in 2012), and an estimated 1.6 million new cases (in 2016) in the US alone.

Numerous therapies have been developed to treat cancer, including for example, surgical removal of the cancer, use of chemotherapeutic drugs (i.e., use of drugs which kill cancer cells), and use of radiation therapy. Nevertheless, it is estimated that in 2016 cancer will kill an estimated 600,000 people in the US alone.

One particularly difficult form of cancer to treat, recurrent glioblasoma (GBM), only has a median survival time of 3 to 7 months. Although surgery for recurrent disease is performed in some patients, it has yet to be established whether surgery alone prolongs survival and/or improves the quality of life for patients with recurrent disease. Furthermore, only two drugs, bevacizumab (Avastin®) and carmustine (Gliadel®) have been approved for recurrent glioblastoma, the latter as an adjunct to surgery. To date, bevacizumab has not been shown to improve survival.

DNX-2401 is currently being investigated for patients with recurrent GBM in several Phase I clinical studies as monotherapy or with other agents. To date, DNX-2401 has been well tolerated with no unexpected clinically significant related toxicity reported across all studies. In the first-in-human Phase I dose-escalating study, no dose-limiting toxicity (DLT) or clinically significant adverse events (AEs) directly related to virus were observed at any dose level. Overall, AEs were generally mild to moderate in severity and considered unrelated to DNX-2401.

The first-in-human Phase I study evaluated intratumoral administration alone (group A) and intratumoral administration followed 14 days later by tumor resection and subsequent intramural delivery (group B) of DNX-2401 throughout the resected tumor cavity. When administered as a single intratumoral injection, 52% of subjects (13 of 25) achieved clinical benefit [complete response (CR)+partial response (PR)+stable disease (SD)] per Macdonald criteria, including 3 durable CRs. The 1-year survival rate for this group was 32% (n=8), regardless of DNX-2401 dose concentration. Four of these 8 subjects (20% overall) survived at least 3 years, including 4 subjects who all achieved a PR (n=1) or CR (n=3). As of February 2016, 3 subjects remain alive 3.8, 4.1, and 4.3 years post-treatment.

Early phase studies with DNX-2401 have demonstrated that the drug has a favorable safety profile and strong tumor-killing potential in patients with recurrent malignant glioma. Additionally, it has been observed that DNX-2401: 1) replicates in human tumors for a period of weeks to months, 2) elicits tumor necrosis within weeks of injection, 3) leads to long-term tumor destruction detectable by Magnetic Resonance Imaging (MRI) and 4) triggers intratumoral immune cell infiltration. Accumulating evidence shows a correlation between tumor-infiltrating lymphocytes (TILs) in cancer tissue and prognosis in various malignancies.$^{i,ii,iii,iv,v,vi,vii,viii,ix,x,xi,xii,xiv}$ Pembrolizumab (KEYTRUDA©), a humanized monoclonal antibody against the programmed death receptor-1 (PD-1) protein, has been developed by Merck & Co. for the treatment of cancer. Pembrolizumab is approved for treatment of melanoma in several countries; in the United States (US) it is indicated for the treatment of advanced, unresectable or metastatic malignant melanoma in patients with disease progression after prior treatment with ipilimumab and, for BRAF V600 mutation-positive patients, a BRAF inhibitor, while in the European Union (EU) it is approved for the treatment of advanced (unresectable or metastatic) melanoma in adults. Pembrolizumab has also been granted approval in the US for the treatment of patients with metastatic non-small cell lung cancer (NSCLC) whose tumors express PD-L1 as determined by an FDA-approved test and who have disease progression on or after platinum-containing chemotherapy. Pembrolizumab has demonstrated initial clinical efficacy in single arm studies as monotherapy for patients with multiple tumor types as determined by response rate. Ongoing clinical trials are being conducted in a number of other advanced solid tumor indications including glioblastoma and hematologic malignancies.

All of the subject matter discussed in the Background is not necessarily prior art and should not be assumed to be prior art merely as a result of its discussion in the Background section. Along these lines, any recognition of problems in the prior art discussed in the Background or associated with such subject matter should not be treated as prior art unless expressly stated to be prior art. Instead, the discussion of any subject matter in the Background should be treated as part of the inventor's approach to the particular problem, which in and of itself, may also be inventive.

SUMMARY

In accordance with the present disclosure, there is provided a method of treating a subject having brain tumor comprising (a) administering an oncolytic adenovirus to said subject; and (b) administering an anti-PD-1 antibody to said subject. The oncolytic adenovirus may be an adenovirus serotype 5 strain, may be selectively replication competent in cells defective in the Rb/p16 tumor suppressor pathway, may contain a deletion of the 24 nucleotides encoding amino acids 122 to 129 of the adenoviral E1A protein, and/or may contain an integrin binding RGD-4C motif. The oncolytic adenovirus may be DNX-2401. The anti-PD1 antibody may be a humanized antibody, such as pembrolizumab. The brain tumor may be glioblastoma multiforme or gliosarcoma. The subject may be a human.

The oncolytic adenovirus is delivered intratumorally, such as via cannula or needle. The oncolytic adenovirus may be delivered at $5 \times 10^8$ viral particles per dose, $5 \times 10^9$ viral particles per dose, or $5 \times 10^{10}$ viral particles per dose. The anti-PD1 antibody may be delivered by intravenous infusion. The anti-PD1 antibody may be delivered at 200 mg per dose. The dose may administered over 30 minutes. A single dose of the oncolytic adenovirus may be is provided prior to three consecutive doses of the anti-PD1 antibody. The time between oncolytic adenovirus administration and the first administration of the anti-PD1 antibody may be about 7-9 days. The time between sequential administrations of the anti-PD1 antibody may be about three weeks.

The method may further comprise administering to the subject one or more of a steroid, an anticonvulsant or an antibody that inhibits vascular endothelial growth factor A. Treating may further comprise additional administrations of the anti-PD1 antibody for up to a 105 weeks or 24 months from the date of oncolytic adenovirus administration. The subject may be evaluated for one of more of overall survival, tumor response, clinical benefit rate, Karnofsky performance status, neurologic status, cytokine levels, lymphocyte levels, or a biomarker, such as PD-1 level or PDL-1 level. Tumor response may be measured by MRI. The method may further comprise stereotactically-guided biopsy of the brain tumor.

The subject may exhibit an overall survival of at least 9 months, 12 months, 15 months, 18 months, 24 months, 36 months or 48 months, any interval therebetween. The subject may exhibit an increase in overall survival, as compared to an untreated control subject, of at least 6 months, 9 months, 12 months, 15 months, 18 months, 24 months, 36 months or 48 months, any interval therebetween. The tumor may exhibit reduced growth, no growth, a 10% reduction in tumor mass, a 20% reduction in tumor mass, a 30% reduction in tumor mass, a 40% reduction in tumor mass, a 50% reduction in tumor mass, a 60% reduction in tumor mass, a 70% reduction in tumor mass, an 80% reduction in tumor mass, a 90% reduction in tumor mass, or a 100% reduction in tumor mass following initiation of treatment. The Karnofsky performance status may measurably and/or statistically improve or remain unchanged following step (b). The subject may exhibit recurrent or progressive brain tumor following previous treatment, such as chemotherapy, radiotherapy, or antibody therapy.

In another embodiment, there is provided a composition comprising (a) an oncolytic adenovirus; and (b) an anti-PD-1 antibody. The oncolytic adenovirus may be an adenovirus serotype 5 strain, and/or may be selectively replication competent in cells defective in the Rb/p16 tumor suppressor pathway, and/or may comprise a deletion of the 24 nucleotides encoding amino acids 122 to 129 of the adenoviral E1A protein, and/or may comprise an integrin binding RGD-4C motif. The oncolytic adenovirus may be DNX-2401. The anti-PD1 antibody may be a humanized antibody, such as pembrolizumab.

The composition may be formulated for intratumoral delivery, or formulated for intravenous infusion. The composition may comprise oncolytic adenovirus in a unit dose of $5 \times 10^8$ viral particles per dose, $5 \times 10^9$ viral particles per dose, or $5 \times 10^{10}$ viral particles per dose. The anti-PD1 antibody may be comprised in a unit dose of 200 mg. The composition may further comprise one or more of a steroid, an anticonvulsant or an antibody that inhibits vascular endothelial growth factor A.

In yet another embodiment, there is provided a composition comprising an oncolytic adenovirus of adenovirus serotype 5 strain, wherein the oncolytic adenovirus is selectively replication competent in cells defective in the Rb/p16 tumor suppressor pathway, wherein the oncolytic adenovirus comprises a deletion of the 24 nucleotides encoding amino acids 122 to 129 of the adenoviral E1A protein, and wherein the oncolytic adenovirus comprises an integrin binding RGD-4C motif. The oncolytic adenovirus may be DNX-2401. The oncolytic adenovirus may be comprised in a unit dose of $5 \times 10^8$ viral particles per dose, a unit dose of $5 \times 10^9$ viral particles per dose, or a unit dose of $5 \times 10^{10}$ viral particles per dose.

Embodiments discussed in the context of methods and/or compositions of the disclosure may be employed with respect to any other method or composition described herein. Thus, an embodiment pertaining to one method or composition may be applied to other methods and compositions of the disclosure as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 2. Study Drug Administration

FIG. 4. Imaging and Treatment after First Radiologic Evidence of Progressive Disease.

FIG. 5. Specific Laboratory Evaluations.

FIGS. 6A and 6B. Pembrolizumab Dose Modification Guidelines for Drug-Related Adverse Events.

DETAILED DESCRIPTION OF THE INVENTION

Figure 1:
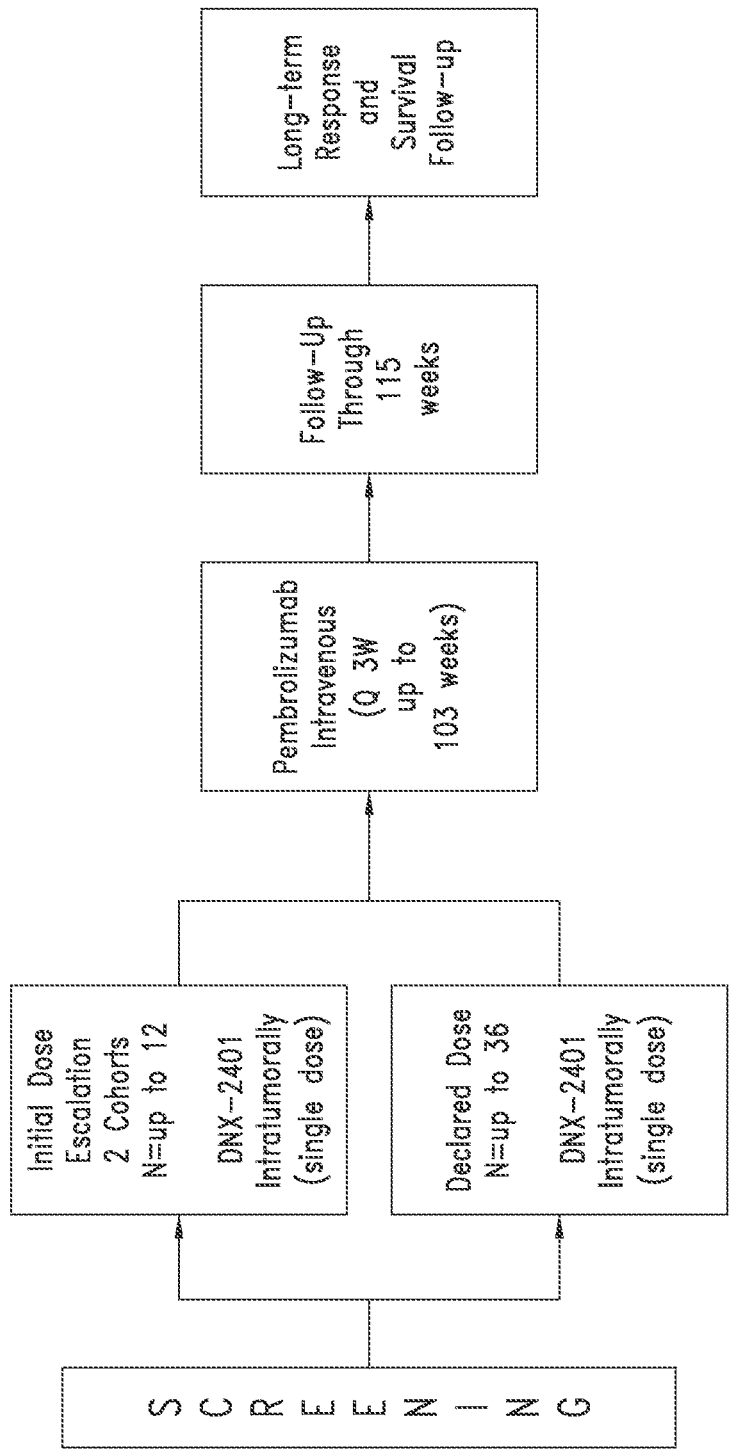
FIG. 1. Overall Study Design.
Figure 3:
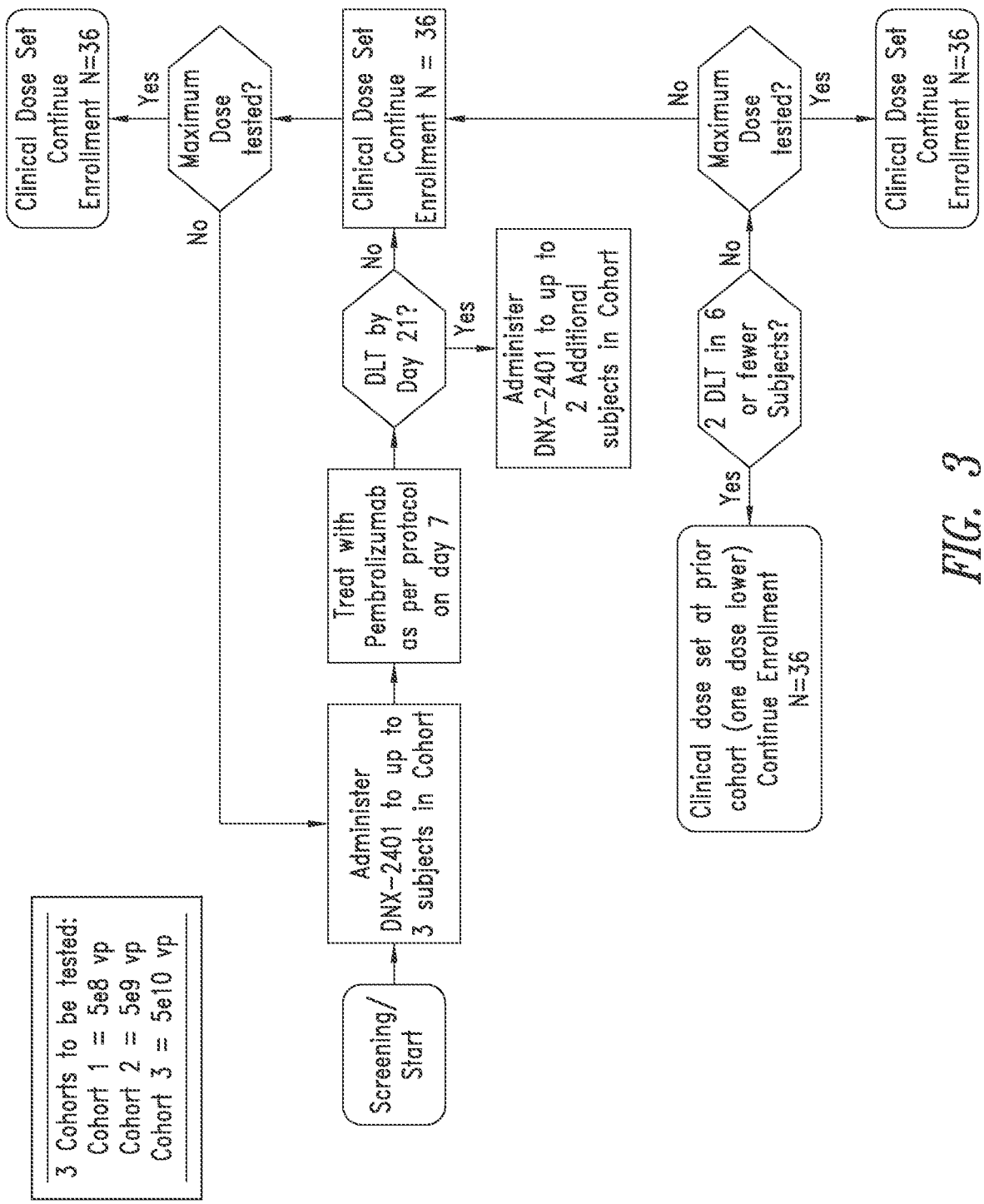
FIG. 3. Dose Limiting Toxicity Study Design.

As discussed above, the present invention provides compositions and methods for treating a cancer (e.g., a brain cancer such as glioblastoma), comprising the step of administering to a subject an oncolytic adenovirus and an anti-PI1 antibody. As is discussed in more detail above, although representative embodiments of an oncolytic adenovirus (e.g., DNX-2401) and an anti-PD1 antibody (e.g., pembrolizumab) have both shown efficacy in distinct types of cancers, they have not been utilized in a clinical setting in concert for a single type of cancer, e.g., brain cancer.

I. CANCER

"Cancer" as utilized herein refers to a large family of diseases characterized by the uncontrolled growth of cells in a body. Representative forms of cancer include carcinomas, sarcomas, myelomas, leukemia's, lymphomas, and mixed types of the above.

Representative forms of cancer include carcinomas, sarcomas, myelomas, leukemia's, lymphomas, and mixed types of the above. Further examples include, but are not limited to bile duct cancer, brain cancers such as glioblastomas, breast cancer, cervical cancer, CNS tumors (such as a glioblastoma, astrocytoma, medulloblastoma, craniopharyogioma, ependymoma, pinealoma, hemangioblastoma, acoustic neuroma, oligodendroglioma, menangioma, neuroblastoma and retinoblastomas), colorectal cancer, endometrial cancer, hematopoietic cell cancers including leukemia's and lymphomas, hepatocellular cancer, kidney cancer, laryngeal cancer, lung cancer, melanoma, oral cancer, ovarian cancer, pancreatic cancer, prostate cancer, squamous cell carcinoma, and thyroid cancer. Cancers may be diffuse (e.g., leukemia's), comprise solid tumors (e.g., sarcomas such as fibrosarcoma, myxosarcoma, liposarcoma, chondrosarcoma and osteogenic sarcoma), or some combination of these (e.g., a metastatic cancer having both solid tumors and disseminated or diffuse cancer cells).

Within particularly preferred embodiments of the invention the cancer is a brain tumor or intracranial neoplasm. All types of brain tumors may produce symptoms that vary depending on the part of the brain involved. These may include headaches, seizures, problem with vision, vomiting, and mental changes. The headache is classically worse in the morning and goes away with vomiting. More specific problems may include difficulty in walking, speaking and with sensation. As the disease progresses unconsciousness may occur.

The cause of most brain tumors is unknown. Risk factors that may occasionally be involved include a number of inherited conditions known as neurofibromatosis as well as exposure to the industrial chemical vinyl chloride, the Epstein-Barr virus, and ionizing radiation. The most common types of primary tumors in adults are: meningiomas (usually benign), and astrocytomas such as glioblastomas. In children, the most common type is a malignant medulloblastoma. Diagnosis is usually by medical examination along with computed tomography or magnetic resonance imaging. This is then often confirmed by a biopsy. Based on the findings, the tumors are divided into different grades of severity.

Treatment may include some combination of surgery, radiation therapy and chemotherapy. Anticonvulsant medication may be needed if seizures occur. Dexamethasone and furosemide may be used to decrease swelling around the tumor. Some tumors grow gradually, requiring only monitoring and possibly needing no further intervention. Treatments that use a person's immune system are being studied. Outcome varies considerably depending on the type of tumor and how far it has spread at diagnosis. Glioblastomas usually have poor outcomes while meningiomas usually have good outcomes. The average five-year survival rate for brain cancer in the United States is 33%.

A. Glioblastoma

Glioblastoma multiforme (GBM), also known as glioblastoma and grade IV astrocytoma, is the most common and most aggressive cancer that begins within the brain. Signs and symptoms are initially non-specific. They may include headaches, personality changes, nausea, and symptoms similar to that of a stroke. Worsening of symptoms is often rapid. This can progress to unconsciousness.

The cause of most cases is unclear. Uncommon risk factors include genetic disorders such as neurofibromatosis and Li Fraumeni syndrome and previous radiation therapy. Glioblastomas represent 15% of brain tumors. They can either start from normal brain cells or develop from an already existing low-grade astrocytoma. The diagnosis is typically made by a combination of CT scan, MRI scan, and tissue biopsy.

There is no clear way to prevent the disease. Typically treatment involves surgery after which chemotherapy and radiation therapy is used. The medication temozolomide is frequently used as part of chemotherapy. High dose steroids may be used to help reduce swelling and decrease symptoms. It is unclear if trying to remove all or simply most of the cancer is better.

Despite maximum treatment, the cancer usually recurs. The most common length of survival following diagnosis is 12 to 15 months with less than 3 to 5% of people surviving greater than five years. Without treatment survival is typically 3 months. About 3 per 100,000 people develop the disease a year. It most often begins around 64 years of age and occurs more commonly in males than females. Immunotherapy is being studied in glioblastoma with promising results.

Although common symptoms of the disease include seizure, nausea and vomiting, headache, memory loss, and hemiparesis, the single most prevalent symptom is a progressive memory, personality, or neurological deficit due to temporal and frontal lobe involvement. The kind of symptoms produced depends highly on the location of the tumor, more so than on its pathological properties. The tumor can start producing symptoms quickly, but occasionally is an asymptomatic condition until it reaches an enormous size.

For unknown reasons, GBM occurs more commonly in males. Most glioblastoma tumors appear to be sporadic, without any genetic predisposition. No links have been found between glioblastoma and smoking, consumption of cured meat, or electromagnetic fields. Alcohol consumption may be a possible risk factor. Glioblastoma has been associated with the viruses SV40, HHV-6, and cytomegalovirus. There also appears to be a small link between ionizing radiation and glioblastoma. Some also believe that there may be a link between polyvinyl chloride (which is commonly used in construction) and glioblastoma. A 2006 analysis links brain cancer to lead exposure in the workplace. There is an association of brain tumor incidence and malaria, suggesting that the *anopheles* mosquito, the carrier of malaria, might transmit a virus or other agent that could cause glioblastoma or that the immunosuppression associated with malaria could enhance viral replication. Also HHV-6 reactivates in response to hypersensitivity reactions from drugs and environmental chemicals. Other risk factors include being male (slightly more common in men than women), being over 50 years old, being Caucasian, Hispanic, or Asian, having a low-grade astrocytoma (brain tumor), which often, given enough time, develops into a higher-grade tumor, or having one of the following genetic disorders is associated with an increased incidence of gliomas: Neurofibromatosis, Tuberous sclerosis, Von Hippel-Lindau disease, Li-Fraumeni syndrome, or Turcot syndrome.

Glioblastoma multiforme tumors are characterized by the presence of small areas of necrotizing tissue that are surrounded by anaplastic cells. This characteristic, as well as the presence of hyperplastic blood vessels, differentiates the tumor from Grade 3 astrocytomas, which do not have these features.

GBMs usually form in the cerebral white matter, grow quickly, and can become very large before producing symptoms. Less than 10% form more slowly following degeneration of low-grade astrocytoma or anaplastic astrocytoma. These are called secondary GBMs and are more common in younger patients (mean age 45 versus 62 years). The tumor may extend into the meninges or ventricular wall, leading to high protein content in the cerebrospinal fluid (CSF) (>100 mg/dL), as well as an occasional pleocytosis of 10 to 100 cells, mostly lymphocytes. Malignant cells carried in the CSF may spread (rarely) to the spinal cord or cause meningeal gliomatosis. However, metastasis of GBM beyond the central nervous system is extremely unusual. About 50% of GBMs occupy more than one lobe of a hemisphere or are bilateral. Tumors of this type usually arise from the cerebrum and may rarely exhibit the classic infiltration across the corpus callosum, producing a butterfly (bilateral) glioma.

The tumor may take on a variety of appearances, depending on the amount of hemorrhage, necrosis, or its age. A CT scan will usually show an inhomogeneous mass with a hypodense center and a variable ring of enhancement surrounded by edema. Mass effect from the tumor and edema may compress the ventricles and cause hydrocephalus.

Four subtypes of glioblastoma have been identified: (i) classical, which includes ninety-seven percent of tumors in the 'classical' subtype carry extra copies of the epidermal growth factor receptor (EGFR) gene, and most have higher than normal expression of epidermal growth factor receptor (EGFR), whereas the gene TP53, which is often mutated in glioblastoma, is rarely mutated in this subtype; (ii) proneural, which often has high rates of alterations in TP53, and in PDGFRA, the gene encoding a-type platelet-derived growth factor receptor, and in IDH1, the gene encoding isocitrate dehydrogenase-1; (iii) mesenchymal, which is characterized by high rates of mutations or other alterations in NF1, the gene encoding Neurofibromin 1 and fewer alterations in the EGFR gene and less expression of EGFR than other types; and (iv) neural, which was typified by the expression of neuron markers such as NEFL, GABRA1, SYT1 and SLC12A5. Many other genetic alterations have been described in glioblastoma, and the majority of them are clustered in three pathways, the P53, RB, and the PI3K/AKT. Glioblastomas have alterations in 64-87%, 68-78% and 88% of these pathways, respectively.

Another important alteration is methylation of MGMT, a "suicide" DNA repair enzyme. Methylation is described to impair DNA transcription and therefore, expression of the MGMT enzyme. Since an MGMT enzyme can only repair one DNA alkylation due to its suicide repair mechanism, reverse capacity is low and methylation of the MGMT gene promoter greatly affects DNA-repair capacity. Indeed, MGMT methylation is associated with an improved response to treatment with DNA-damaging chemotherapeutics, such as temozolomide.

Cancer cells with stem cell-like properties have been found in glioblastomas (this may be a cause of their resistance to conventional treatments, and high recurrence rate). These so-called glioblastoma stem-like cells reside in a niche around arterioles, which protects these cells against therapy by maintaining a relatively hypoxic environment. A biomarker for cells in glioblastomas that exhibit cancer stem cell properties, the transcription factor Hes3, has been shown to regulate their number when placed in culture.

The IDH1 gene encodes for the enzyme isocitrate dehydrogenase 1 and is frequently mutated in glioblastoma (primary GBM: 5%, secondary GBM>80%). By producing very high concentrations of the "oncometabolite" D-2-hydroxyglutarate and dysregulating the function of the wild-type IDH1-enzyme it induces profound changes to the metabolism of IDH1-mutated glioblastoma, compared with IDH1 wild-type glioblastoma or healthy astrocytes. Among others, it increases the glioblastoma cells' dependence on glutamine or glutamate as an energy source. It has been hypothesized that IDH1-mutated glioblastoma are in a very high demand for glutamate and use this amino acid and neurotransmitter as a chemotactic signal. Since healthy astrocytes excrete glutamate, IDH1-mutated glioblastoma cells do not favor dense tumor structures but instead migrate, invade and disperse into healthy parts of the brain where glutamate concentrations are higher. This may explain the invasive behaviour of these IDH1-mutated glioblastoma.

Furthermore, glioblastoma multiforme exhibits numerous alterations in genes that encode for ion channels, including upregulation of gBK potassium channels and ClC-3 chloride channels. It has been hypothesized that by upregulating these ion channels, glioblastoma tumor cells can facilitate increased ion movement over the cell membrane, thereby increasing $H_2O$ movement through osmosis, which aids glioblastoma cells in changing cellular volume very rapidly. This is helpful in their extremely aggressive invasive behavior, because quick adaptations in cellular volume can facilitate movement through the sinuous extracellular matrix of the brain.

When viewed with MRI, glioblastomas often appear as ring-enhancing lesions. The appearance is not specific, however, as other lesions such as abscess, metastasis, tumefactive multiple sclerosis, and other entities may have a similar appearance. Definitive diagnosis of a suspected GBM on CT or MRI requires a stereotactic biopsy or a craniotomy with tumor resection and pathologic confirmation. Because the tumor grade is based upon the most malignant portion of the tumor, biopsy or subtotal tumor resection can result in undergrading of the lesion. Imaging of tumor blood flow using perfusion MRI and measuring tumor metabolite concentration with MR spectroscopy may add value to standard MRI in select cases by showing increased relative cerebral blood volume and increased choline peak respectively, but pathology remains the gold standard for diagnosis and molecular characterization.

It is important to distinguish primary glioblastoma from secondary glioblastoma. These tumors occur spontaneously (de novo) or have progressed from a lower-grade glioma, respectively. Primary glioblastomas have a worse prognosis, different tumor biology and may have a different response to therapy, which makes this a critical evaluation to determine patient prognosis and therapy. Over 80% of secondary glioblastoma carries a mutation in IDH1, whereas this mutation is rare in primary glioblastoma (5-10%). Thus, IDH1 mutations are a useful tool to distinguish primary and secondary glioblastomas since histopathologically they are very similar and the distinction without molecular biomarkers is unreliable.

It is very difficult to treat glioblastoma due to several complicating factors. For example, the tumor cells are very resistant to conventional therapies, the brain is susceptible to damage due to conventional therapy, the brain has a very limited capacity to repair itself, many drugs cannot cross the blood-brain barrier to act on the tumor, and treatment of primary brain tumors and brain metastases consists of both symptomatic and palliative therapies.

Supportive treatment focuses on relieving symptoms and improving the patient's neurologic function. The primary supportive agents are anticonvulsants and corticosteroids.

Historically, around 90% of patients with glioblastoma underwent anticonvulsant treatment, although it has been estimated that only approximately 40% of patients required this treatment. Recently, it has been recommended that neurosurgeons not administer anticonvulsants prophylactically, and should wait until a seizure occurs before prescribing this medication. Those receiving phenytoin concurrent with radiation may have serious skin reactions such as erythema multiforme and Stevens-Johnson syndrome.

Corticosteroids, usually dexamethasone given 4 to 8 mg every 4 to 6 h, can reduce peritumoral edema (through rearrangement of the blood-brain barrier), diminishing mass effect and lowering intracranial pressure, with a decrease in headache or drowsiness.

Palliative treatment usually is conducted to improve quality of life and to achieve a longer survival time. It includes surgery, radiation therapy, and chemotherapy. A maximally feasible resection with maximal tumor-free margins is usually performed along with external beam radiation and chemotherapy. Gross total resection of tumor is associated with a better prognosis.

Surgery is the first stage of treatment of glioblastoma. An average GBM tumor contains $10^{11}$ cells, which is on average reduced to $10^9$ cells after surgery (a reduction of 99%). Benefits of surgery include resection for a pathological diagnosis, alleviation of symptoms related to mass effect, and potentially removing disease before secondary resistance to radiotherapy and chemotherapy occurs.

The greater the extent of tumor removal, the better. Removal of 98% or more of the tumor has been associated with a significantly longer healthier time than if less than 98% of the tumor is removed in retrospective analyses. The chances of near-complete initial removal of the tumor may be increased if the surgery is guided by a fluorescent dye known as 5-aminolevulinic acid. GBM cells are widely infiltrative through the brain at diagnosis, and so despite a "total resection" of all obvious tumor, most people with GBM later develop recurrent tumors either near the original site or at more distant locations within the brain. Other modalities, typically radiation and chemotherapy, are used after surgery in an effort to suppress and slow recurrent disease.

Subsequent to surgery, radiotherapy becomes the mainstay of treatment for people with glioblastoma. It is typically performed along with giving temozolomide (TMZ). A pivotal clinical trial carried out in the early 1970s showed that among 303 GBM patients randomized to radiation or non-radiation therapy, those who received radiation had a median survival more than double those who did not. Subsequent clinical research has attempted to build on the backbone of surgery followed by radiation. On average, radiotherapy after surgery can reduce the tumor size to $10^7$ cells. Whole-brain radiotherapy does not improve when compared to the more precise and targeted three-dimensional conformal radiotherapy. A total radiation dose of 60-65 Gy has been found to be optimal for treatment.

GBM tumors are well known to contain zones of tissue exhibiting hypoxia which are highly resistant to radiotherapy. Various approaches to chemotherapy radiosensitizers have been pursued with limited success. As of 2010, newer research-approaches included preclinical and clinical investigations into the use of an oxygen diffusion-enhancing compound such as trans-sodium crocetinate (TSC) as radiosensitizers, and as of 2015 a clinical trial was underway.

Boron neutron capture therapy has been tested as an alternative treatment for glioblastoma multiforme but is not in common use.

Most studies show no benefit from the addition of chemotherapy. However, a large clinical trial of 575 participants randomized to standard radiation versus radiation plus temozolomide chemotherapy showed that the group receiving temozolomide survived a median of 14.6 months as opposed to 12.1 months for the group receiving radiation alone. This treatment regime is now standard for most cases of glioblastoma where the person is not enrolled in a clinical trial. Temozolomide seems to work by sensitizing the tumor cells to radiation.

High doses of temozolomide in high-grade gliomas yield low toxicity, but the results are comparable to the standard doses. Antiangiogenic therapy with medications such as bevacizumab control symptoms but do not affect overall survival.

Alternating electric field therapy is an FDA-approved therapy for newly diagnosed and recurrent glioblastoma. In 2015, initial results from a phase-three randomized clinical trial of alternating electric field therapy plus temozolomide in newly diagnosed glioblastoma reported a three-month improvement in progression-free survival, and a five-month improvement in overall survival compared to temozolomide therapy alone, representing the first large trial in a decade to show a survival improvement in this setting. Despite these results, the efficacy of this approach remains controversial among medical experts.

The median survival time from the time of diagnosis without any treatment is 3 months, but with treatment survival of 1-2 years is common. Increasing age (>60 years of age) carries a worse prognostic risk. Death is usually due to widespread tumor infiltration with cerebral edema and increased intracranial pressure.

A good initial Karnofsky Performance Score (KPS) and MGMT methylation are associated with longer survival. A DNA test can be conducted on glioblastomas to determine whether or not the promoter of the MGMT gene is methylated. Patients with a methylated MGMT promoter have longer survival than those with an unmethylated MGMT promoter, due in part to increased sensitivity to temozolomide. This DNA characteristic is intrinsic to the patient and currently cannot be altered externally. Another positive prognostic marker for glioblastoma patients is mutation of the IDH1 gene, which can be tested by DNA-based methods or by immunohistochemistry using an antibody against the most common mutation, namely IDH1-R132H.

More prognostic power can be obtained by combining the mutational status of IDH1 and the methylation status of MGMT into a two-gene predictor. Patients with both IDH1 mutations and MGMT methylation have the longest survival, patients with an IDH1 mutation or MGMT methylation an intermediate survival and patients without either genetic event have the shortest survival.

Long-term benefits have also been associated with those patients who receive surgery, radiotherapy, and temozolomide chemotherapy. However, much remains unknown about why some patients survive longer with glioblastoma. Age of under 50 is linked to longer survival in glioblastoma multiforme, as is 98%+ resection and use of temozolomide chemotherapy and better Karnofsky performance scores. A recent study confirms that younger age is associated with a much better prognosis, with a small fraction of patients under 40 years of age achieving a population-based cure. The population-based cure is thought to occur when a population's risk of death returns to that of the normal population, and in GBM, this is thought to occur after 10 years.

B. Gliosarcoma

Gliosarcoma is a rare type of glioma, a cancer of the brain that comes from glial, or supportive, brain cells, as opposed to the neural brain cells. Gliosarcoma is a malignant cancer, and is defined as a glioblastoma consisting of gliomatous and sarcomatous components.

It is estimated that approximately 2.1% of all glioblastomas are gliosarcomas. Although most gliomas rarely show metastases outside the cerebrum, gliosarcomas have a propensity to do so, most commonly spreading through the blood to the lungs, and also liver and lymph nodes.

Knowledge about this entity is limited to small retrospective case series and case reports. In general, the epidemiology and natural history of GSM appears similar to glioblastoma (GBM). No patient or treatment factors have been unequivocally identified that distinguish outcomes of GSM from GBM. Gliosarcomas have an epidemiology similar to that of glioblastomas, with the average age of onset being 54 years, and males being affected twice as often as females. They are most commonly present in the temporal lobe.

Due to small patient numbers, available case series are not sufficiently powered to precisely characterize GSM. Modest, yet clinically meaningful, differences between GSM and GBM may surface with examination of a larger series. To refine our understanding of GSM, we used the Surveillance, Epidemiology, and End Results (SEER) database to identify and analyze more than 300 adult GSM patients and compare them to adult GBM patients.

II. ACTIVE AGENTS

A. Oncolytic Adenoviruses

"Adenovirus" (Ad) refers to a large (approximately 36 kb) DNA virus that infects humans, but which also display a broad host range. Physically, adenovirus is an icosahedral virus containing a double-stranded, linear DNA genome. There are approximately 50 serotypes of human adenoviruses, which are divided into six families based on molecular, immunological, and functional criteria. By adulthood, virtually every human has been infected with the more common adenovirus serotypes, the major effect being cold-like symptoms.

Adenoviral infection of host cells results in adenoviral DNA being maintained episomally, which reduces the potential genotoxicity associated with integrating vectors. In addition, adenoviruses are structurally stable, and no genome rearrangement has been detected after extensive amplification. Adenovirus can infect most epithelial cells regardless of their cell cycle stage. So far, adenoviral infection appears to be linked only to mild disease such as acute respiratory disease in humans.

Members of any of the 57 human adenovirus serotypes (HAdV-1 to 57) may incorporate heterologous nucleic acid encoding an immune cell stimulatory receptor agonist according to the invention. Human Ad5 is well characterized genetically and biochemically (GenBank M73260; AC 000008). Thus, in a preferred embodiment, the oncolytic adenovirus is a replication competent Ad5 serotype or a hybrid serotype comprising an Ad5 component. The adenovirus may be a wild type strain but is preferably genetically modified to enhance tumor selectivity, for example by attenuating the ability of the virus to replicate within normal quiescent cells without affecting the ability of the virus to replicate in tumor cells. Non-limiting examples of replication competent oncolytic adenoviruses encompassed by the present invention include Delta-24, Delta-24-RGD, ICOVIR-5, ICOVIR-7, ONYX-015, ColoAd1, H101 and AD5/3-D24-GMCSF. Onyx-015 is a hybrid of virus serotype Ad2 and Ad5 with deletions in the E1B-55K and E3B regions to enhance cancer selectivity. H101 is a modified version of Onyx-015. ICOVIR-5 and ICOVIR-7 comprise an Rb-binding site deletion of E1A and a replacement of the E1A promoter by an E2F promoter. ColoAd1 is a chimeric Ad11p/Ad3 serotype. AD5/3-D24-GMCSF (CGTG-102) is a serotype 5/3 capsid-modified adenovirus encoding GM-CSF (the Ad5 capsid protein knob is replaced with a knob domain from serotype 3).

Oncolytic adenoviruses injected into a tumor induce cell death and release of new adenovirus progeny that, by infecting the neighbor cells, generates a treatment wave that, if not halted, may lead to the total destruction of the tumor. Significant antitumor effects of Delta-24 have been shown in cell culture systems and in malignant glioma xenograft models. Delta-24-RGD has shown surprising anti-tumor effects in a Phase I clinical trial and is currently the subject of additional clinical trials. Although lysis of tumor cells is the main anti-cancer mechanism proposed for Delta-24-RGD oncolytic adenovirus, data from the Phase I clinical trial in patients with recurrent glioma and other observations indicate that the direct oncolytic effect may be enhanced by the adenovirus-mediated trigger of anti-tumor immune response.

The infectious cycle of the adenovirus takes place in 2 steps: the early phase which precedes initiation of the replication of the adenoviral genome, and which permits production of the regulatory proteins and proteins involved in the replication and transcription of the viral DNA, and the late phase which leads to the synthesis of the structural proteins. The early genes are distributed in 4 regions that are dispersed in the adenoviral genome, designated E1 to E4 ("E" denotes "early"). The early regions comprise at least-six transcription units, each of which possesses its own promoter. The expression of the early genes is itself regulated, some genes being expressed before others. Three regions, E1, E2, and E4 are essential to replication of the virus. Thus, if an adenovirus is defective for one of these functions this protein will have to be supplied in trans, or the virus cannot replicate.

The E1 early region is located at the 5' end of the adenoviral genome, and contains 2 viral transcription units, E1A and E1B. This region encodes proteins that participate very early in the viral cycle and are essential to the expression of almost all the other genes of the adenovirus. In particular, the E1A transcription unit codes for a protein that transactivates the transcription of the other viral genes, inducing transcription from the promoters of the E1B, E2A, E2B, E3, and E4 regions and the late genes.

Within one embodiment of the invention, one or more heterologous sequences can be incorporated into a nonessential region of the adenovirus. Within a particularly preferred embodiment of the invention one or more heterologous sequences can be integrated in place of all or part of the E3 region. Representative examples include cytokines, chemokines and checkpoint inhibitors. Within one embodiment the heterologous sequence code for an OX40 agonist (e.g., OX40L), GITR, anti-PD-1, and/or anti-CTLA-3. Within another embodiment the heterologous nucleic acid sequence encodes an inhibitor of an immune checkpoint protein selected from the group consisting of CTLA4, PID-I, PD-LI, PD-L2, B7-H3, B7-H4, TIM3, GAL9, LAG3, VISTA, KIR, and/or BTLA. Within yet another embodiment the heterologous nucleic acid sequence encodes an agonist of an immune co-stimulatory receptor selected from the group consisting of CD28, OX40 (CD 134), glucocorticoid-induced TNF-receptor (GITR), CD137 (4-1BB), herpes virus entry mediator A (HVEM), inducible T-cell costimulator (Icos or cD278), cD27, CD40, and/or CD226. Representative examples are disclosed in more detail in PCT/US2014/066920 and U.S. Provisional No. 62/342,482, filed May 27, 2016, both of which are incorporated by reference in their entirety.

The adenovirus enters the permissive host cell via a cell surface receptor, and it is then internalized. The viral DNA associated with certain viral proteins needed for the first steps of the replication cycle enters the nucleus of the infected cells, where transcription is initiated. Replication of the adenoviral DNA takes place in the nucleus of the infected cells and does not require cell replication. New viral particles or virions are assembled after which they are released from the infected cells, and can infect other permissive cells.

The adenovirus is an attractive delivery system. Embodiments of the invention can utilize manufacturing process with maximum yields of $1\times10^5$ viral particles per cell. The process can be free of or essentially free of protein, serum, and animal derived components making it suitable for a broad range of both prophylactic and therapeutic vaccine products.

Several factors favor the use of oncolytic adenoviruses for the treatment of brain tumors. First, gliomas are typically localized, and therefore an efficient local approach should be sufficient to cure the disease without any detrimental effects on other parts of the body. Second, gliomas harbor several populations of cells expressing different genetic abnormalities. Thus, the spectrum of tumors sensitive to the transfer of a single therapeutic gene to cancer cells may be limited. Third, replication competent adenoviruses can infect and destroy cancer cells that are arrested in $G_0$. Since gliomas invariably include non-cycling cells, this property is important. Finally, the p16-Rb pathway is abnormal in the majority of gliomas, thus making Delta-24 adenovirus particularly effective for treating these tumors, although the loss of the retinoblastoma tumor suppressor gene function has been associated with the causes of various types of tumors and is not limited to treatment of gliomas. The oncolytic adenoviruses of the instant invention are replication-competent in cells with a mutant Rb pathways.

If an adenovirus has been mutated so that it is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. In certain aspects a helper cell line is 293. Various methods of culturing host and helper cells may be found in the art, for example (Racher, A. J., Fooks, A. R. & Griffiths, J. B. Biotechnol Tech (1995) 9: 169.)

Adenoviruses can be isolated using different methodologies. Most often, after transfection of the Ad genome, adenoviral plaques are isolated from the agarose overlaid cells and the viral particles are expanded for analysis. For detailed protocols the skilled artisan is referred to (Graham, F. L., and Prevec, L. (1991). Manipulation of adenovirus vectors. Methods Mol Biol 7, 109-128).

Alternative technologies for the generation of adenovirus vectors include utilization of the bacterial artificial chromosome (BAC) system, in vivo bacterial recombination in a recA+ bacterial strain utilizing two plasmids containing complementary adenoviral sequences, and the yeast artificial chromosome (YAC) system (PCT publications 95/27071 and 96/33280, which are incorporated herein by reference).

Representative examples of adenovirus vectors suitable for use within the present invention include those described in US Publication Nos. 2009/0175830, 2014/0377221, 2014/0377294, 2015/0306160, 2016/0289645, and 2016/0143967, and U.S. Pat. Nos. 6,210,946, 6,284,742, 6,312,699, 6,555,368, 6,649,396, 6,815,200, 6,824,771, 6,841,540, 6,955,808, 7,045,348, 7,297,542, 8,168,168 and 9,061,055, all of which are incorporated by reference in their entirety.

III. DNX-2401

In one particularly preferred embodiment, the replication competent oncolytic adenovirus is Delta-24 or Delta-24-RGD. Delta-24 is described in U.S. Patent Application Publication Nos. 20030138405, and 20060147420, each of which are incorporated herein by reference (see also ""). The Delta-24 adenovirus is derived from adenovirus type 5 (Ad-5) and contains a 24-base-pair deletion within the CR2 portion of the E1A gene that encompasses the area responsible for binding Rb protein (nucleotides 923-946) corresponding to amino acids 122 to 129 in the encoded E1A protein (Fueyo J et al., Oncogene, 19:2-12 (2000)). Delta-24-RGD further comprises an insertion of the RGD-4C sequence (which binds strongly to avB3 and avB5 integrins) into the HI loop of the fiber knob protein (Pasqualini R. et al., Nat Biotechnol, 15:542-546 (1997)). The E1A deletion increases the selectivity of the virus for cancer cells; the RGD-4C sequence increases the infectivity of the virus for gliomas and for several other tumors which express low level of adenovirus receptors.

A. Therapeutic Uses

A stereotactic or image-guided injection device guides the delivery of DNX-2401 into the tumor through a small hole in the skull. The virus establishes an active infection by replicating in and killing tumor cells with high potency and specificity. Results from Phase I clinical studies indicate that DNX-2401: (i) can replicate in human tumors for a period of weeks to months, (ii) can elicit tumor necrosis within weeks of injection, (iii) can trigger intratumoral immune cell infiltration, and (iv) can lead to long term tumor destruction detectable by MRI.

DNX-2401 has been well tolerated. To date, it is associated with limited toxicity as noted during several completed or ongoing Phase I clinical studies investigating DNX-2401 as a single agent or together with other agents for recurrent disease. The maximum dose evaluated in a first-in-human Phase I trial for subjects with recurrent glioma was 3e10 vp without any dose-limiting toxicity reported (Study ID01-310). Clinical benefit (CR+PR+SD) was observed in 52% (n=13) of the subjects enrolled (n=25) in the intratumoral injection group (group A) of the study, based on Investigator-assessed MRI. Overall, 28% of subjects achieved a CR (n=3) or PR (n=4). The subject that achieved a complete response at the lowest dose level for any responding subject (1e8 vp) remains alive 4.2 years following DNX-2401 treatment. In a subset of subjects, pseudo-progression noted on MRI was observed prior to tumor regression, similar to objective response kinetics observed with several other immunotherapies. The 1-year survival rate for this group was 32% (n=8), irrespective of DNX-2401 dose. Encouragingly, four of these 8 subjects (20% overall) survived at least 3 years, including 4 subjects who achieved a PR (n=1) or CR (n=3). As of February 2016, 3 subjects remain alive 3.8, 4.1, and 4.3 years post-treatment. (Refer to the current Investigator's Brochure for further updates)

DNX-2401 contains two stable genetic changes in the adenovirus dsDNA genome that cause it to (1) replicate selectively in Rb-pathway deficient cells and (2) infect cells that express RGD-binding integrins more efficiently. A deletion of 24 bases in the E1A gene and insertion of an integrin-binding motif (RGD) in the H1 loop of the fiber accomplished this. Because virtually all tumor cells, including GBM, harbor defects in the Rb pathway or are already in the cell cycle, DNX-2401 replicates in and kills these tumor cells selectively and efficiently. DNX-2401 is superior to wild type adenovirus with respect to replication in rapidly growing tumor cells, an unprecedented property for an oncolytic virus.[xvii,xviii,xxiv]

B. Clinical Experience in Glioma

Study ID01-310. DNX-2401 was evaluated in a first in human, two-group, dose-escalating Phase I study (Study ID01-310) in 37 subjects with recurrent high-grade malignant glioma at a single center; The University of Texas MD Anderson Cancer Center. Group A investigated a single direct intratumoral injection of DNX-2401 into recurrent tumor without further resection (n=25). Group B investigated a biological endpoint that was to demonstrate intratumoral virus replication and included only subjects with resectable tumors (n=12). These subjects received two injections; an initial intratumoral injection into biopsy-confirmed glioma on Day 0, followed 14 days later by tumor resection and subsequent injection of a divided dose of DNX-2401 into the post-resection tumor bed.

Safety.

No dose-limiting toxicity (DLT) was reported during clinical study ID01-310 at any dose level, including the highest dose evaluated (3e10 vp), and there have been no clinically significant unexpected DNX-2401-related safety concerns observed to date in ongoing Phase I studies with 3e10 vp. Therefore, a maximum tolerated dose (MTD) was not reached prior to study completion. Adverse events were generally mild to moderate in severity, and unrelated to virus following both types of administration (i.e., intratumoral and intramural). Analysis of subject sera, saliva, nasopharyngeal secretions and urine did not demonstrate any significant virus shedding. Only one serious adverse event report of Grade 1 headache/head pain, Grade 1 confusion and Grade 2 fever was considered possibly related to virus for one subject. All deaths were considered unrelated to DNX-2401.

Efficacy.

Although study ID01-310 was a dose-escalation study designed to evaluate a dose concentration of DNX-2401 that spanned four orders of magnitude, all subjects were included in the secondary efficacy analysis.

In group A (n=25, intratumoral injection), subjects were enrolled across 8 dose cohorts (1e7 to 3e10 vp). Clinical benefit (as measured by CR+PR+SD) was seen in 52% of subjects (n=13), including 28% who achieved a best response of PR (n=4) or CR (n=3). The subject that achieved a complete response at the lowest dose level for any responding subject (1e8 vp) remains alive 4.2 years following DNX-2401 treatment. In a subset of subjects, pseudo-progression noted on MRI was observed prior to tumor regression, similar to objective response kinetics observed with several other immunotherapies.[xxi] The 1-year survival rate for this group was 32% (n=8), irrespective of DNX-2401 dose. Four of these 8 subjects (20% overall) survived at least 3 years, including 4 subjects that all achieved a PR (n=1) or CR (n=3). As of February 2016, 3 subjects remain alive 3.8, 4.1, and 4.3 years post-treatment.

In group B (n=12, intratumoral (within the tumor) and intramural (tumor bed) injection; biological endpoint arm), subjects were enrolled across 4 dose cohorts (1e7 to 3e8 vp; total exposure after two injection: 2e7 to 6e8 vp). Subjects (n=12) completed treatment successfully. Because tumor resection was part of the treatment plan for group B, only a limited number of subjects (25%, 3 of 12) had measurable disease 14 days following intratumoral injection, which would have been essential to evaluate changes in tumor burden and response per investigator assessment. Of these 3 subjects, a best response of PR was achieved for 1 subject (33%) and SD for 2 subjects (67%). Nine subjects (75%) had no measurable disease as a result of surgery and were not considered evaluable for clinical response.

Immune Response to DNX-2401.

An immunological evaluation of resected tumors after DNX-2401 treatment was conducted on a subset of subjects, based on tumor availability. Two tumors from subjects enrolled in group A (intratumoral injection) were resected several months after DNX-2401 administration in response to what appeared to be tumor progression or pseudo-progression. In both instances, pathologists reported that the tumors were 80% and 90% necrotic with the remaining tumor infiltrated by immune cells, including CD4 and CD8 T-cells. Analysis of resected tumors from subjects enrolled in group B (intratumoral and intramural injection) provided further evidence of tumor infiltration by macrophages at two weeks, followed by the influx of T cells after several months. Overall, this dynamic immune response may account for the persistence of anti-glioma effects as well as the delayed treatment effect observed during this study.

Study D24GBM.

Study D24GBM is an ongoing single center, Phase I, Investigator-sponsored study being conducted at the University Clinic of Navarra (Spain). The study is investigating a single dose of 3e10 vp of DNX-2401 followed two weeks later by dose-dense temozolomide administered for 8 weeks in subjects with glioblastoma at first recurrence. Subjects receive either 1) a single intratumoral injection during biopsy without further resection, 2) an intramural injection and injection into the resection cavity after tumor resection, or 3) an intratumoral injection of partially resected tumor with injection into the resected cavity. As of November 2015, all 31 planned subjects have received DNX-2401. Based on preliminary data, no significant safety findings related to DNX-2401 have been observed.

Study 2401BT-IFN-001.

Study 2401BT-IFN-001 (TARGET I) is an ongoing, randomized, multi-center Phase Ib trial to investigate the safety of administering 3e10 vp DNX-2401 into recurrent tumor followed 2 weeks later by treatment with gamma interferon in subjects with recurrent glioblastoma or gliosarcoma. Enrolled subjects are randomized to either DNX-2401 with interferon-gamma or to DNX-2401 alone in a 2:1 manner. As of March 2016, 26 of 24-36 evaluable subjects have been enrolled. The protocol was amended to include delivery of DNX-2401 by a cannula at a dose of 5e10 vp to a subset of subjects. Preliminary data is not yet available.

C. Clinical Experience in Other Indications

Study 0643.

DNX-2401 has also been evaluated systemically in a completed single-center, Phase I study in subjects (n=21) with recurrent malignant gynecologic disease conducted as an Investigator-sponsored study at the University of Alabama at Birmingham. The study evaluated the feasibility and utility of intraperitoneally delivered DNX-2401 for subjects with recurrent epithelial ovarian cancer who had persistent or recurrent disease following debulking and paclitaxel/platinum-based chemotherapy. Cohorts of eligible subjects were treated with virus for three days that was administered via an intraperitoneal catheter, to determine the MTD. No DLTs were observed and an MTD was not reached with the highest DNX-2401 dose tested: 1e12 vp/day for 3 days. No vector-related Grade 3 or 4 toxicities were reported, and no clinically significant laboratory abnormalities were noted. Adverse events were limited to Grade 1/2 fever, fatigue, or abdominal pain. Overall, AEs were considered unlikely or unrelated to virus and deemed to be associated with underlying disease or the route of delivery. Viral shedding studies showed insignificant shedding in the serum, saliva, and urine. The maximum tolerated dose was not reached. Over a one-month follow-up, 15 (71%) patients had stable disease and six (29%) had progressive disease. Seven patients had a decrease in CA-125; four had a drop>20%.

D. DNX-2401 Dosing

An MTD was not reached in Phase I studies. The potential additive effects of intratumoral DNX-2401, followed by intravenous pembrolizumab treatment are not known. Therefore, an initial phase of dose escalation consisting of 3-cohorts (5e8 vp, 5e9 vp, and 5e10 vp; up to 12 subjects, total) to determine a safe intratumoral dose of DNX-2401 in association with pembrolizumab is justified. Single and repeat administration of DNX-2401 has been well tolerated in multiple animal toxicity studies (e.g., MTD of ICB 7.5e10 vp in cotton rats) and early phase human studies (ID01-310, D24GBM; preliminary 2401BT-IFN-001). In addition, intraperitoneal DNX-2401 administered at a dose of up 1e12 vp/day for 3 consecutive days has been shown to be well tolerated in humans. Modifications to declared dose, volume, timing, may be necessary in certain circumstances; however, changes will require approval from a Medical Monitor or designee prior to implementation.

E. Method of Delivery

DNX-2401 is a conditionally replicative virus capable of replication in tumor cells; however, the vector does not replicate in surrounding normal brain tissue. Experience has shown that direct intratumoral injection of DNX-2401 is safe and effective for delivering DNX-2401 into the target tumor and increases the potential of tumor cell exposure to the virus. Based on this evidence, direct intratumoral administration of DNX-2401 via the Alcyone MEMS Cannula (AMCT) was selected for this Phase II study to optimize virus delivery and provide a standardized technique.

In a particular aspect, replication competent adenoviruses are delivered via intratumoral injection into the brain. Direct injection into the brain may be accomplished by a fine catheter or cannula. With certain embodiments, the replication competent oncolytic adenoviruses can be delivered by a microelectromechanical (MEMS) system under MR intra-procedural guidance. In particular, intratumoral injection into the brain is accomplished without significant reflux or backflow by using cannula such as Alcyone Lifesciences' Alcyone MEMS Cannula (AMC). Representative examples of devices are described in U.S. Pat. No. 8,992,458 and U.S. Patent Publications 2013/0035660, 2013/0035574 and 2013/0035560, each of which are hereby incorporated by reference in their entirety.

F. Anti-PD-1 Therapeutics

Binding of PD-L1 on tumor cells to PD-1 on activated effector T cells results in activation of PI3 kinase-signaling cascade which in turn blocks the production of cytotoxic mediators required for killing tumor cells. As used herein, a PD-L1 or PD-1 antagonist is a molecule that disrupts the interaction between PD-L1 and PD-1. In one aspect, the anti-PD-1 therapeutic is an antibody. Representative examples include the anti-PD-L1 antibody MPDL3280A, or an anti-PD-1 antibody such as nivolumab (Opdivo—Bristol Myers Squibb), or, lambrolizumab. Within another embodiment the anti-PD-1 therapeutic is Pembrolizumab (as is discussed in more detail below. Other drugs in early stage development targeting PD-1 receptors (checkpoint inhibitors) are Pidilizumab (CT-011, Cure Tech) and BMS-936559 (Bristol Myers Squibb). Both Atezolizumab (MPDL3280A, Roche) and Avelumab (Merck KGaA, Darmstadt, Germany & Pfizer) target the similar PD-L1 receptor.

Other anti-PD-1 therapeutics that can be delivered include those described in US Patent Application Publication Nos. 2009/0217401, 20110195068 and 20120251537 and U.S. Pat. No. 8,217,149, the contents of each which are incorporated herein by reference.

IV. PEMBROLIZUMAB

Pembrolizumab (KEYTRUDA®), a humanized monoclonal antibody against the programmed death receptor-1 (PD-1) protein, has been developed by Merck & Co. for the treatment of cancer. Pembrolizumab is approved for treatment of melanoma in several countries; in the US it is indicated for the treatment of advanced, unresectable or metastatic malignant melanoma in patients with disease progression after prior treatment with ipilimumab and, for BRAF V600 mutation-positive patients, a BRAF inhibitor, while in the EU it is approved for the treatment of advanced (unresectable or metastatic) melanoma in adults. Pembrolizumab has also been granted approval in the US for the treatment of patients with metastatic NSCLC whose tumors express PD-L1 as determined by an FDA-approved test and who have disease progression on or after platinum-containing chemotherapy.

Pembrolizumab has demonstrated initial clinical efficacy in single arm monotherapy trials in subjects with multiple tumor types as determined by response rate. Ongoing clinical trials are being conducted in a number of other advanced solid tumor indications and hematologic malignancies.

A. Pharmaceutical and Therapeutic Background

The importance of intact immune surveillance in controlling outgrowth of neoplastic transformation has been known for decades. Accumulating evidence shows a correlation between tumor-infiltrating lymphocytes (TILs) in cancer tissue and prognosis in various malignancies.[i,ii,iii,iv,v,vi,vii,viii,ix,x,xi,xii,xiii] In particular, the presence of CD8+ T cells and the increased ratio of CD8+ effector T cells/FoxP3+ regulatory T cells seem to correlate with improved prognosis and long-term survival in many solid tumors.[xxvii,xxvii,xxix,xxx,xxxi,xxxii]

The PD-1 receptor-ligand interaction is a major pathway hijacked by tumors to suppress immune control. The normal function of PD-1, expressed on the cell surface of activated T cells under healthy conditions, is to down-modulate unwanted or excessive immune responses, including auto-immune reactions. PD-1 (encoded by the gene Pdcd1) is an Ig superfamily member related to CD28 and CTLA-4, which has been shown to negatively regulate antigen receptor signaling upon engagement of its ligands (PD-L1 and/or PD-L2). The structures of murine PD-1 alone and in complex with its ligands were first resolved and more recently the NMR-based structure of the human PD-1 extracellular region and analyses of its interactions with its ligands were also reported. PD-1 and family members are type I transmembrane glycoproteins containing an Ig Variable-type (V-type) domain responsible for ligand binding and a cytoplasmic tail which is responsible for the binding of signaling molecules. The cytoplasmic tail of PD-1 contains 2 tyrosine-based signaling motifs, an immunoreceptor tyrosine-based inhibition motif (ITIM) and an immunoreceptor tyrosine-based switch motif (ITSM). Following T cell stimulation, PD-1 recruits the tyrosine phosphatases SHP-1 and SHP-2 to the ITSM motif within its cytoplasmic tail, leading to the dephosphorylation of effector molecules, such as CD3ζ, PKCθ and ZAP70, which are involved in the CD3 T cell signaling cascade. The mechanism by which PD-1 down-modulates T cell responses is similar to, but distinct from that of CTLA-4. PD-1 was shown to be expressed on activated lymphocytes, including peripheral CD4+ and CD8+ T cells, B cells, T regs and Natural Killer cells. Expression has also been shown during thymic development on CD4−CD8− (double-negative) T cells, as well as subsets of macrophages and dendritic cells. The ligands for PD-1 (PD-L1 and PD-L2) are constitutively expressed or can be induced in a variety of cell types. PD-L1 is expressed at low levels on various non-hematopoietic tissues, most notably on vascular endothelium, whereas PD-L2 protein is only detectably expressed on antigen-presenting cells found in lymphoid tissue or chronic inflammatory environments.[xliv] Both ligands are type I transmembrane receptors containing both IgV- and IgC-like domains in the extracellular region and short cytoplasmic regions with no known signaling motifs. Binding of either PD-1 ligand to PD-1 inhibits T cell activation triggered through the T cell receptor. PD-L2 is thought to control immune T cell activation in lymphoid organs, whereas PD-L1 serves to dampen unwarranted T cell function in peripheral tissues. Although healthy organs express little, if any, PD-L1, a variety of cancers were demonstrated to express abundant levels of this T cell inhibitor, which, via its interaction with the PD-1 receptor on tumor-specific T cells, plays a critical role in immune evasion by tumors. As a consequence, the PD-1/PD-L1 pathway is an attractive target for therapeutic intervention in cancer.

B. Non-Clinical Studies with Pembrolizumab

Therapeutic studies in mouse models have shown that administration of antibodies blocking PD-1/PD-L1 interaction enhances infiltration of tumor-specific CD8+ T cells and ultimately leads to tumor rejection, either as a monotherapy or in combination with other treatment modalities.[xlix,l,li,lii,liii,iv,lv] Anti-mouse PD-1 or anti-mouse PD-L1 antibodies have demonstrated antitumor responses in models of squamous cell carcinoma, pancreatic carcinoma, melanoma, acute myeloid leukemia and colorectal carcinoma.[lii,liv,lv] In such studies, tumor infiltration by CD8+ T cells and increased IFN-γ, granzyme B and perforin expression were observed, indicating that the mechanism underlying the antitumor activity of PD-1 checkpoint inhibition involved local infiltration and activation of effector T cell function in vivo.[liv] Experiments have confirmed the in vivo efficacy of anti-mouse PD-1 antibody as a monotherapy, as well as in combination with chemotherapy, in syngeneic mouse tumor models.

C. Pembrolizumab Dose Selection

The dose of pembrolizumab to be studied in this trial is 200 mg given intravenously every 3 weeks (Q3W). The dose recently approved in the United States and several other countries for treatment of melanoma subjects is 2 mg/kg Q3W. Information on the rationale for selecting 200 mg Q3W is summarized below.

In KEYNOTE-001, an open-label Phase I study conducted to evaluate the safety, tolerability, pharmacokinetics (PK), pharmacodynamics (PD), and anti-tumor activity of pembrolizumab when administered as monotherapy. The dose escalation portion of this trial evaluated three dose levels, 1 mg/kg, 3 mg/kg and 10 mg/kg, administered every 2 weeks (Q2W) and dose expansion cohorts evaluated 2 mg/kg Q3W and 10 mg/kg Q3W in subjects with advanced solid tumors. All dose levels were well tolerated and no dose-limiting toxicities were observed. This first-in-human study of pembrolizumab showed evidence of target engagement and objective evidence of tumor size reduction at all dose levels. No maximum tolerated dose (MTD) has been identified. In addition, two randomized cohort evaluations of melanoma subjects receiving pembrolizumab at a dose of 2 mg/kg versus 10 mg/kg Q3W have been completed, and one randomized cohort evaluating 10 mg/kg Q3W versus 10 mg/kg Q2W has also been completed. The clinical efficacy and safety data demonstrate a lack of important differences in efficacy or safety profile across doses.

An integrated body of evidence suggests that 200 mg every 3 weeks (Q3W) is expected to provide similar response to 2 mg/kg Q3W, 10 mg/kg Q3W and 10 mg/kg Q2W. Previously, a flat pembrolizumab exposure-response relationship for efficacy and safety has been found in subjects with melanoma in the range of doses between 2 mg/kg and 10 mg/kg. Exposures for 200 mg Q3W are expected to lie within this range and will be close to those obtained with 2 mg/kg Q3W dose.

A population pharmacokinetic (PK) model, which characterized the influence of body weight and other patient covariates on exposure, has been developed. The PK profile of pembrolizumab is consistent with that of other humanized monoclonal antibodies, which typically have a low clearance and a limited volume of distribution. The distribution of exposures from the 200 mg fixed dose are predicted to considerably overlap those obtained with the 2 mg/kg dose and importantly will maintain individual patient exposures within the exposure range established in melanoma as associated with maximal clinical response. Pharmacokinetic properties of pembrolizumab, and specifically the weight-dependency in clearance and volume of distribution are consistent with no meaningful advantage to weight-based dosing relative to fixed dosing.

In translating to other tumor indications, similarly flat exposure-response relationships for efficacy and safety as observed in subjects with melanoma can be expected, as the anti-tumor effect of pembrolizumab is driven through immune system activation rather than through a direct interaction with tumor cells, rendering it independent of the specific tumor type. In addition, available PK results in subjects with melanoma, NSCLC, and other tumor types support a lack of meaningful difference in pharmacokinetic exposures obtained at tested doses among tumor types. Thus the 200 mg Q3W fixed-dose regimen is considered an appropriate fixed dose for other tumor indications as well.

A fixed dose regimen will simplify the dosing regimen to be more convenient for physicians and to reduce potential for dosing errors. A fixed dosing scheme will also reduce complexity in the logistical chain at treatment facilities and reduce wastage. The existing data suggest 200 mg Q3W as the appropriate dose for pembrolizumab.

D. Commercial Dosage Forms

There are currently two formulations of KEYTRUDA®. KEYTRUDA® for injection is a sterile, preservative-free, and white to off-white lyophilized powder in single-use vials. Each vial is reconstituted and diluted for intravenous infusion. Each 2 mL of reconstituted solution contains 50 mg of pembrolizumab formulated in L-histidine (3.1 mg), polysorbate 80 (0.4 mg), and sucrose (140 mg) and may contain hydrochloric acid/sodium hydroxide to adjust pH to 5.5. KEYTRUDA® solution for injection is a sterile, preservative-free, clear to slightly opalescent, colorless to slightly yellow solution that requires dilution for intravenous infusion. Each vial contains 100 mg of pembrolizumab in 4 mL of solution. Each 1 mL of solution contains 25 mg of pembrolizumab formulated in: L-histidine (1.55 mg), polysorbate 80 (0.2 mg), sucrose (70 mg), and water for injection, USP.

V. SUBJECTS

An evaluable subject is defined as an eligible subject who receives at least one dose, or part of one dose, of study drug (DNX-2401 and pembrolizumab) and one who completes the Day 28 study visit.

Subjects who discontinue study participation for any reason, other than progressive disease or study treatment-related toxicity, prior to completing the Day 28 study visit, will not be evaluable and will be replaced but will continue to be monitored for safety and survival.

Subjects in general should meet the following inclusion criteria for treatment.

≥18 years of age on the day of informed consent

A single glioblastoma or gliosarcoma tumor with histopathological confirmation (if a prior diagnosis exists such as anaplastic astrocytoma, or other tumor types that have progressed to GBM, inclusion may be allowed following discussion with a Medical Monitor or designee)

Subjects with contiguous tumors may be eligible with approval

First or presenting second recurrence of glioblastoma or gliosarcoma at the time of consent Gross total or partial tumor resection, including tumor debulking, is not possible or planned A single measurable tumor that is at least 10.0 mm longest diameter (LDi)×10.0 mm shortest diameter (SDi) and this tumor does not exceed 40.0 mm in LDi or SDi The measurable area of the tumor is solid/nodular and is not cystic (most tumors will have cystic components and subjects who have a tumor that is partially cystic may be eligible for the study with approval or if the surgeon can perform an injection within the measurable solid parts of the tumor)

Willing to provide a tumor tissue sample for biomarker analysis and mutational status from an archived slide or newly obtained stereotactic core biopsy Tumors must be accessible for stereotactic injection Confirmatory evidence of tumor recurrence (e.g., progression after last treatment) on the screening MRI 15 days to minus 72 hours, inclusive, prior to planned start time Tumor wherein the location will not risk delivery of virus into the ventricular system Tumor recurrence or progression documented after previously failing surgical resection, chemotherapy and/or radiation Resolution of toxic effect(s) of the most recent prior chemotherapy to Grade 1 or less (except neuropathy and alopecia)

Note: Subjects with ≤Grade 2 neuropathy and/or alopecia are an exception to this criterion and they will not be excluded for these reasons alone.

Demonstrate adequate organ function as defined below:
Hematological
Absolute neutrophil count (ANC)≥1,500/mcL
WBC≥2.5×10$^3$/mm$^3$
Platelets≥100,000/mcL
Hemoglobin≥10 g/dL or ≥5.6 mmol/L
Renal
Creatinine≤1.5×ULN
BUN≤1.5×ULN
Hepatic
Total bilirubin≤1.5×ULN or Direct bilirubin≤ULN for subjects with total bilirubin levels>1.5×ULN
AST (SGOT) and ALT (SGPT)≤2.5×ULN
Coagulation
International Normalized Ratio (INR)≤1.5×ULN
Prothrombin Time (PT)≤1.5×ULN
Activated Partial Thromboplastin Time (aPTT)≤1.5× ULN
Adequate venous access
Karnofsky performance status≥70%
Afebrile at baseline/Day 0 prior to DNX-2401 administration (i.e., <38.0° C.)

Prior anti-tumor therapies must have been completed within the following time periods prior to DNX-2401 injection:
4 weeks after nitrosoureas
2 weeks after vincristine
3 weeks after procarbazine or temozolomide
4 weeks after bevacizumab, other antibody therapy or other anti-angiogenic therapy to treat glioblastoma
5 half-lives for other anti-cancer agents including investigational agents (or 2 weeks after the last dose when the half-life is unknown). A discussion of these agents will take place with a Medical Monitor or designee prior to establishing eligibility.
For applicable screening candidates, external beam radiotherapy (>5000 cGy) must have been completed at least 12 weeks prior to DNX-2401 administration Females should not be pregnant and should take steps to remain non-pregnant, such as by using twice the normal protection of birth control (i.e., double-barrier) by using a condom and spermicidal jelly or foam, or a diaphragm and spermicidal jelly or foam. A spermicidal jelly or foam should be used in addition to a barrier method (e.g., condom or diaphragm). Male subjects should use an acceptable method of contraception throughout the study starting with DNX-2401 administration through 180 days after the single dose of DNX-2401 and 120 days after the last dose of pembrolizumab.

Patients must be willing and able to provide informed consent, undergo and comply with all study assessments and adhere to the protocol schedule, and agree not to donate blood or gametes following virus administration.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLES

Example 1

Study Parameters

Objectives.

Primary objectives are to evaluate the safety of escalating doses of DNX-2401 and the overall safety of the declared dose of intratumoral DNX-2401 when followed by sequential intravenous administration of pembrolizumab, and to determine the objective response rate (ORR). Secondary objectives are to determine overall survival (OS-12) and to determine the clinical benefit rate (CBR; defined as CR+PR+SD) per RANO criteria and RANO criteria modified to account for pseudo-progression (e.g., iRANO). Exploratory objectives are to evaluate overall survival (OS), OS-8, progression free survival (PFS), progression free survival at six months (PFS-6), time to tumor response, duration of response, per RANO criteria and RANO criteria modified to account for pseudo-progression (e.g., iRANO), to evaluate changes in Karnofsky performance status (KPS) and neurologic status, and to evaluate cytokines, lymphocyte sub-types and other potential biomarkers (e.g., PD-1, PD-L1 expression, genetic mutation).

Subjects. Inclusion criteria are set forth above. Exclusion criteria are as follows:

Recurrent GBM with multiple (≥2) separate enhancing tumors (measurable or non-measurable)

Tumor shape that is bi-lobular or multifocal

Tumor involvement that would require ventricular, brainstem or posterior fossa injection or access through a ventricle or risk of ventricular penetration in order to deliver DNX-2401

Tumor involves both hemispheres or involves the sub-ependyma or suspected cerebrospinal fluid (CSF) dissemination (extension of the tumor across the midline of the corpus callosum is consistent with contralateral hemisphere (bi-hemispheric) involvement which is prohibited)

Documented extracranial metastases

Requires treatment with high-dose systemic corticosteroids defined as dexamethasone>4 mg/day or bioequivalent for at least 3 consecutive days within 2 weeks of start of pembrolizumab (an alternative management strategy may be considered following prior consideration)

Uncontrolled blood-sugar levels defined as HbA1c>7% on 2 separate measurements

Active autoimmune disease that requires, or has required, systemic treatment in the past 2 years (i.e., with use of disease-modifying agents, corticosteroids or immunosuppressive drugs) or replacement therapy (e.g., thyroxine, insulin, or physiologic corticosteroid replacement therapy for adrenal or pituitary insufficiency, etc.) is not considered a form of systemic treatment Previous treatment with anti-PD1 or PD-L1 agents including pembrolizumab Evidence of active, non-infectious pneumonitis A history of interstitial lung disease Transfusions or medications (e.g., G-CSF) to treat pancytopenia or other hematological conditions within 4 weeks prior to DNX-2401 administration Prior gene transfer therapy or prior therapy with a cytolytic virus of any type Live vaccines of any kind within 45 days prior to DNX-2401 administration and while participating in the study other than seasonal influenza killed virus vaccines for injection Major surgery within 4 weeks and minor surgery within 2 weeks of DNX-2401 administration (if subject received major surgery, they must have fully recovered from the toxicity and/or complications from the intervention prior to receiving DNX-2401)

Currently participating and receiving investigational agent(s) or has participated in a study of an investigational agent(s) and received investigational agent(s) or used an investigational device within 30 days prior to DNX-2401 administration Any contraindication for undergoing MRI Is pregnant or breastfeeding, or expecting to conceive or father children during the study, starting with the screening visit through 180 days after the single dose of DNX-2401 and 120 days after the last dose of pembrolizumab Evidence of active uncontrolled infection or an unstable or severe intercurrent medical condition that requires treatment and/or precludes surgery History of prior malignancy except for curatively treated basal or squamous cell carcinoma of the skin (non-melanoma skin cancer), cervical or vaginal intra-epithelial neoplasia, non-invasive breast cancer in situ or localized prostate cancer with a current prostate-specific antigen (PSA) of <4.0 ng/mL (mcg/L) (subjects with other curatively treated malignancies who have had no evidence of metastatic disease and a >2 year disease-free interval may be enrolled after approval)

Any medical condition that precludes intratumoral injection into the brain tumor Immunocompromised subjects or those with autoimmune conditions, active hepatitis (HAV, HBV, HCV), known history of active TB (*Mycobacterium tuberculosis*), or human immunodeficiency virus (HIV) seropositivity (TB testing is required for subjects recently exposed to persons with active tuberculosis or who have traveled recently to areas where TB is endemic)

Active hepatitis B is defined as anti-HBc core antibody and HBsAg surface antigen positivity Evidence of bleeding diathesis or use of anticoagulant medication or any medication that may increase the risk of bleeding that cannot be stopped more one week prior to surgery (low weight heparin and drugs in the anticoagulant class (e.g., Lovenox (enoxaparin) administered on a temporary, limited basis for post-procedure deep vein thrombosis (DVT) prophylaxis are permitted)

Encephalitis, multiple sclerosis or other central nervous system (CNS) infection or primary CNS disease that would interfere with subject evaluation Li-Fraumeni Syndrome or with a known germ line defect in the retinoblastoma gene or its related pathways Significant systemic or major illnesses including but not limited to: congestive heart failure, ischemic heart disease, kidney disease or renal failure, or organ transplantation Alcohol or substance abuse or alcohol dependency that is active within 12 months prior to screening that has caused health consequences History or current diagnosis of any medical or psychological condition that in the Investigator's opinion, might interfere with the subject's ability to participate in the study or the inability to obtain informed consent because of cognitive, psychiatric or complicating medical problems Study Duration.

Up to 105 weeks of treatment (approximately 24 months) with follow-up through 90 days following the final dose of pembrolizumab. Thereafter, long-term survival follow-up will be performed every 16 weeks for response, survival, study drug-related adverse events and adverse events resulting in death.

Study Design.

The protocol involves a single intratumoral administration of DNX-2401 with sequentially administered intravenous pembrolizumab for subjects with first or second glioblastoma or gliosarcoma recurrence for whom gross total or partial resection is not possible or planned. In the initial phase of the study, up to a total of 12 eligible subjects will participate in the dose-escalation process and will be enrolled using a 3+3 study design in dose-escalating cohorts as follows:

Cohort 1: Single dose DNX-2401 ($5\times10^8$ vp) delivered intratumorally followed by sequential intravenous pembrolizumab every 3 weeks (Q3W)

Cohort 2: Single dose DNX-2401 ($5\times10^9$ vp) delivered intratumorally followed by sequential intravenous pembrolizumab every 3 weeks (Q3W)

Cohort 3: Single dose DNX-2401 ($5\times10^{10}$ vp) delivered intratumorally followed by sequential intravenous pembrolizumab every 3 weeks (Q3W)

Three (3) subjects will be enrolled in Cohort 1 and will be followed for 21 days after the initial dose of pembrolizumab for evaluation of dose-limiting toxicity (DLT). If no DLTs are observed, and following a review of clinical data (e.g., laboratory results, adverse events), the next cohort will be enrolled. If, in any cohort, 1 DLT is observed out of the initial 3 subjects, then 3 additional subjects will be added to the same cohort. The dose escalation will continue until at least 2 subjects experience DLTs or the highest dose cohort of $5\times.10^{10}$ vp is completed and all subjects have been closely monitored for safety for 21 days following administration of the first dose of pembrolizumab on Day 7. If 2 or more subjects have a DLT, then the previous dose will be considered the declared Phase 2 dose. If, after safety review of all dosed cohorts, there are no DLTs in the first 3 subjects or <2 DLTs in the expanded cohort of 6 subjects, this cohort will be deemed safe and tolerable.

Following the initial enrollment and dose-determination phase, enrollment will continue at the declared dose for up to 36 additional eligible subjects. These subjects will receive a single intratumoral DNX-2401 dose via cannula on Day 0, or via needle, and managed per the institution's standard policy for post-operative care. All subjects who enroll will also begin pembrolizumab infusions 7-9 days following administration of DNX-2401.

Prior to virus delivery, a stereotactically-guided biopsy of the tumor will be obtained and analyzed via frozen section to confirm the presence of recurrent tumor at the planned intratumoral injection target. In addition to histopathological analysis, the tissue will be analyzed for mutational status, other potential biomarkers, and archived.

Pembrolizumab will be infused intravenously at a dose of 200 mg over 30 minutes every 3 weeks beginning on Day 7 (+2-day window) and continuing for up to 105 weeks or until progressive disease is confirmed. On Day 7, if subjects are experiencing any AEs following the DNX-2401 administration procedure on Day 0, the AEs must be ≤Grade 1 or returned to baseline status prior to receiving the first dose of intravenous pembrolizumab.

Subjects who complete the treatment phase and End of Study visit will be subsequently monitored through Week 115 (i.e., 12 weeks or 90 days following final dose of pembrolizumab at Week 103). End of study, post-pembrolizumab interval safety status will be reviewed at the first long-term survival follow-up visit (Week 119). Thereafter, subjects will be followed for response, survival, study drug-related adverse events, and adverse events resulting in death (regardless of relationship) every 16 weeks.

Subjects who withdraw or terminate from the study early will have an assessment of adverse events and serious adverse events (including Events of Clinical Interest (ECI)) for 90 days post-study drug administration or 30 days post-study drug administration if anti-cancer therapy is initiated. Thereafter, subjects will be followed for response, survival, study drug-related adverse events, and adverse events resulting in death (regardless of relationship) every 8 weeks.

Safety monitoring will be performed throughout the study. Monitoring will include adverse events and serious adverse events (including Events of Clinical Interest (ECI)), laboratory evaluations, physical and neurological examinations, vital sign measurements, and MRI, including the post-DNX-2401 injection procedure MRI (within 36 hours post DNX-2401 administration) to assess for hematoma.

Additionally, other exploratory assessments may include changes in cytokines, lymphocyte sub-types and other potential biomarkers (e.g., PD-1 and PD-L1). Changes in KPS, and neurologic status will also be evaluated.

Tumor response will be determined by MRI performed every 4 weeks up to Week 28. The Week 28 visit corresponds to approximately 6 months post-DNX-2401 administration and may take place no sooner than 182 days following Day 0. In support of this, the Week 28 (Cycle 10) visit is conducted between 194 and 198 days post-DNX-2401 administration. After Week 28 (Month 6) tumor response will continue to be followed with MRI every 8 weeks until Week 105 (approximately 24 months) post-DNX-2401 and every 16 weeks thereafter (long-term survival follow-up). Because DNX-2401 appears to work, at least in part, by eliciting an antitumor immune response, objective response will be evaluated by RANO criteria and RANO criteria modified to account for pseudo-progression (e.g., iRANO).

In addition to Investigator assessments, MR images will be collected for independent central review. Partial and complete responses will be confirmed at a minimum of 4 weeks later (28 days+3-day window) by repeat MRI. In the case of suspected progressive disease by MRI, a confirmatory MRI will be performed at a minimum of 4 weeks later (28 days+3-day window). The neuroradiologist or other qualified PI-designee will make tumor measurements and assessments required for clinical treatment decisions. In the event of progressive disease on MRI in a subject who is clinically stable, the investigator may exercise discretion by keeping the subject on-study. Because tumor regression has been demonstrated >5 months or later, following the intratumoral delivery of DNX-2401, every effort should be made to manage clinical signs and symptoms before initiating an alternative therapy.

If necessary, each subject should receive the lowest possible stable steroid dose for 7 days prior to DNX-2401 administration and for 3 days prior to any response/disease assessment MRI. For suspected autoimmune events or conditions and pseudoprogression and/or tumor swelling (e.g., appearance of central nervous system (CNS) symptoms or worsening thereof), pulse-dosing of steroids (e.g., 4 mg BID×3 days, then 4 mg daily×2 days, then off) is recommended.

During the two weeks preceding the first dose of pembrolizumab, steroids are to be restricted and may not exceed 4 mg dexamethasone per day for 3 consecutive days within 2 weeks prior to the first dose of pembrolizumab on study Day 7 (+2-day window) per protocol eligibility exclusion criterion. Following completion of the Week 4 (Day 28) study visit, in the event that pulse-dosing with steroids is not effective in the control of tumor swelling/edema, low-dose (3-5 mg/kg every 2 weeks×3) bevacizumab (Avastin®) may be used at the Principal Investigator's discretion to address cerebral edema in lieu of systemic steroid administration.

If bevacizumab (Avastin®) is used to address cerebral edema, the lowest possible stable dose should be used for 3 days prior to any response/disease assessment MRI. Avastin® should not be initiated within 28 days before or after Day 0/surgery to administer DNX-2401 or subsequent surgery for other reasons due to known complications in surgery/wound healing and hemorrhage.

Anticonvulsants may also be administered to manage and prevent seizures in subjects with a pre-existing medical history of seizures, otherwise they should not be administered prophylactically.

Safety Assessments.

Safety assessments will include: collection of adverse event and serious adverse event data (including Events of Clinical Interest (ECI)), physical and neurological examinations, laboratory examinations, vital signs measurements, and MRI (including the MRI obtained within 36 hours post DNX-2401 administration to assess for possible post-procedure hematoma). The safety reporting period begins at Informed Consent for SAEs and Day 0 for AEs and continues through 12 weeks (90 days) after the last dose of study drug. Study drug-related adverse events and adverse events that result in death (regardless of relationship) will be reported from Day 0 and through long-term survival follow-up every 16 weeks (every 8 weeks for cases of early termination).

Statistical Methods. Sample Size:

Up to a total of 48 evaluable subjects may be enrolled. In the initial dose escalation phase, the safety and incidence of dose limiting toxicities (DLTs) that occur within 21 days post the first infusion of pembrolizumab for each cohort will be summarized.

The primary endpoint [objective response rate (ORR)] defined as a complete response (CR) or a partial response (PR), will be tested in a single arm (group) design. The sample size estimation was based on a historical control response rate equal to 5%.[lvii,viii] The null hypothesis to be tested is that the DNX-2401 treated population has the same ORR as the historical control rate. A one-sided test with an alpha=0.05 and N of 36 (declared Phase 2 dose) will yield 80% power for an alternative hypothesis of ORR=18%.

Analysis Sets:

Safety Analysis Set (SAS): This set will include subjects who receive at least one dose (or part of one dose) of study drug (DNX-2401 and/or pembrolizumab). Typically the SAS would include subjects who do not have measurable tumor at baseline; however, to be eligible for the study, all subjects must have measurable disease.

Evaluable Analysis Set (EAS):

Based on the intent-to-treat principle, this set will include subjects who receive at least one dose (or part of one dose) of DNX-2401 and pembrolizumab and who have measurable tumor at baseline.

Safety Analyses:

All safety analyses will be performed on the Safety Analysis Set. Adverse events (AEs) will be graded according to Version 4.03 (Jun. 14, 2010) of the National Cancer Institute-Common Terminology Criteria for Adverse Events (NCI-CTCAE), or according to a protocol-defined severity scale determined by the Investigator for events not listed in the CTCAE. DNX-2401 treatment-emergent AEs are those defined as having an onset after the start time of DNX-2401 administration and continue through week 105 (approximately 24 months) or Early Termination, whichever occurs first. Pembrolizumab treatment-emergent AEs are those defined as having an onset after the first dose of pembrolizumab up through 90 days after the last dose of pembrolizumab or Early Termination (whichever comes first). Treatment-emergent AEs for DNX-2401 and pembrolizumab will be summarized separately using the most current version of the Medical Dictionary for Regulatory Activities (MedDRA) by System Organ Class (SOC) and Preferred Term (PT), classified from Investigator-reported verbatim terms. The number and percentage of subjects with at least one occurrence of a preferred term will be summarized, according to the most severe grade using a 5-point scale (Grade 1-5). The number of events per preferred term will also be summarized. Maximum severity and causality (relationship to study drug) will be summarized separately.

The number and percentage of subjects reporting AEs, SAEs, related AEs, related SAEs, ≥Grade 3 AEs, related ≥Grade 3 AEs, and AEs leading to withdrawal, or treatment discontinuation will be summarized by dose according to SOC and preferred term. AEs will also be presented in subject listings. The duration of AEs will be determined and included in listings, along with the action taken and outcome. Subject listings and narratives will also be provided for SAEs, AEs resulting in discontinuation, and death.

Medical history and concurrent illnesses will be summarized and may be examined as potential confounders in the treatment-response relationship. Prior and concomitant medications and therapies will be coded using the latest version of the World Health Organization Drug Dictionary (WHO-DD) and will be summarized.

Laboratory results will be classified according to NCI-CTCAE and summarized by parameter and by time point. Laboratory results not corresponding to a coded term will not be graded. The incidence of laboratory abnormalities will be summarized. The worst on-study grade after DNX-2401 administration and after pembrolizumab will be summarized. The incidence of ≥Grade 3 laboratory abnormalities and shifts in toxicity grading from baseline to highest grade post-baseline will also be displayed. Laboratory values will be listed by subject and values outside of a normal reference range will be flagged. Pregnancy test results will be listed separately.

Vital sign measurements will be summarized by visit using descriptive statistics. Physical examination findings will be summarized by visit and will also be presented in subject listings.

Efficacy Analyses:

All efficacy analyses will be performed on the Evaluable Analysis Set (EAS). The primary efficacy endpoint will be the objective response rate (ORR), defined as the sum (and percent) of those subjects with a complete response (CR) or partial response (PR) as the best overall response recorded from the start of treatment until progressive disease or at the latest time point obtained.

Objective response determined from MRI review will be based upon the RANO criteria and RANO criteria modified to account for pseudo-progression (e.g., iRANO) with the primary analysis based on RANO criteria (as assessed by the central reader). ORR will be summarized by the number and percentage of subjects. Corresponding 95% and 90% confidence intervals (CIs) will be based upon the binomial exact method.

Complete, partial responses and suspected progression will be confirmed. Any partial or complete response noted on MRI will be confirmed by repeat MRI at a minimum of 4 weeks (28 days with +3-day window) later. In the case of suspected tumor progression by MRI, and with the absence of deteriorating clinical status as determined by the Investigator, a repeat MRI will be performed, if possible, at a minimum of 4 weeks (28 days with +3-day window) later in an attempt to confirm progressive disease. In the case of suspected progressive disease, confirmation by tumor biopsy is strongly recommended. Additionally, if the tumor is resected prior to initiating an alternative cancer therapy, tissue should also be collected for histopathology, molecular assays (e.g., sequencing, gene expression, immunohistochemistry) and archived for future analysis related to this study.

Secondary efficacy endpoints will include OS-12 and CBR. OS-12 will be summarized using Kaplan-Meier (KM) methods; all estimates will be presented with 95% confidence intervals. CBR will be summarized as the number and proportion of subjects with clinical benefit, along with 95% CIs for the proportion of subjects with clinical benefit based on the binomial exact method.

Additional efficacy endpoints will be summarized based on the EAS. Other exploratory efficacy endpoints will include: OS, OS-8, PFS, PFS-6, time to response, duration of response per RANO criteria and RANO criteria modified to account for pseudo-progression (e.g., iRANO). All such endpoints will be summarized using Kaplan-Meier methods with estimates presented along with 95% CIs.

OS-8 and OS-12 will be presented as 8-month and 12-month survival estimates along with 95% CIs. The OS endpoint is defined as the overall survival profile of all subjects while on study and will be summarized with KM survival curves as well as quartile estimates (25%, median, 75%) and associated 95% CIs.

Population subgroup analyses (e.g., cytokines, lymphocyte sub-types, if performed) may be determined and subgroup analyses performed. In addition, correlation analyses based on parameters such as immunological effects may also be performed.

Changes from baseline in KPS and neurologic status will also be summarized at each time point by subject.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A method of treating a subject having brain tumor comprising:
   (a) administering an oncolytic adenovirus to said subject; and
   (b) administering an anti-PD-1 antibody to said subject.
2) The method of embodiment 1, wherein the oncolytic adenovirus is an adenovirus serotype 5 strain, is selectively replication competent in cells defective in the Rb/p16 tumor suppressor pathway, contains a deletion of the 24 nucleotides encoding amino acids 122 to 129 of the adenoviral E1A protein, and/or contains an integrin binding RGD-4C motif.
3) The method of embodiments 1-2, wherein the oncolytic adenovirus is DNX-2401.
4) The method of embodiments 1-3, wherein the anti-PD1 antibody is a humanized antibody.
5) The method of embodiments 1-4, wherein the anti-PD1 antibody is pembrolizumab.
6) The method of embodiments 1-5, wherein the oncolytic adenovirus is delivered intratumorally.
7) The method of embodiment 6, wherein the oncolytic adenovirus is delivered via cannula or needle.
8) The method of embodiments 1-7, wherein the oncolytic adenovirus is delivered at $5\times10^8$ viral particles per dose, $5\times10^9$ viral particles per dose, or $5\times10^{10}$ viral particles per dose.
9) The method of embodiments 1-8, wherein the anti-PD1 antibody is delivered by intravenous infusion.
10) The method of embodiments 1-9, wherein the anti-PD1 antibody is delivered at 200 mg per dose.
11) The method of embodiment 10, wherein the dose is administered over 30 minutes.
12) The method of embodiments 1-11, wherein a single dose of the oncolytic adenovirus is provided prior to three consecutive doses of the anti-PD1 antibody.
13) The method of embodiment 12, wherein the time between oncolytic adenovirus administration and the first administration of the anti-PD1 antibody is about 7-9 days.
14) The method of embodiments 12-13, wherein the time between sequential administrations of the anti-PD1 antibody is about three weeks.
15) The method of embodiments 1-14, further comprising administering to the subject one or more of a steroid, an anticonvulsant or an antibody that inhibits vascular endothelial growth factor A.
16) The method of embodiment 12, wherein treating further comprises additional administrations of the anti-PD1 antibody for up to a 105 weeks or 24 months from the date of oncolytic adenovirus administration.
17) The method of embodiments 1-16, wherein said subject is evaluated for one of more of overall survival, tumor response, clinical benefit rate, Karnofsky performance status, neurologic status, cytokine levels, lymphocyte levels, or a biomarker.

18) The method of embodiment 17, wherein said biomarker is PD-1 level or PDL-1 level.
19) The method of embodiment 18, wherein tumor response is measured by MRI.
20) The method of embodiments 1-19, further comprising stereotactically-guided biopsy of the brain tumor.
21) The method of embodiments 1-20, wherein the brain tumor is glioblastoma multiforme.
22) The method of embodiments 1-20, wherein the brain tumor is gliosarcoma.
23) The method of embodiments 1-22, wherein the subject exhibits an overall survival of at least 9 months, 12 months, 15 months, 18 months, 24 months, 36 months or 48 months, any interval therebetween.
24) The method of embodiments 1-22, wherein the subject exhibits an increase in overall survival, as compared to an untreated control subject, of at least 6 months, 9 months, 12 months, 15 months, 18 months, 24 months, 36 months or 48 months, any interval therebetween.
25) The method of embodiments 1-22, wherein the tumor exhibits reduced growth, no growth, a 10% reduction in tumor mass, a 20% reduction in tumor mass, a 30% reduction in tumor mass, a 40% reduction in tumor mass, a 50% reduction in tumor mass, a 60% reduction in tumor mass, a 70% reduction in tumor mass, an 80% reduction in tumor mass, a 90% reduction in tumor mass, or a 100% reduction in tumor mass following initiation of treatment.
26) The method of embodiments 1-22, wherein the Karnofsky performance status improves or remains unchanged following step (b).
27) The method of embodiments 1-22, wherein there is a statistically measurable clinical benefit.
28) The method of embodiments 1-27, wherein the subject exhibits recurrent or progressive brain tumor following previous treatment.
29) The method of embodiments 1-28, wherein the previous treatment was chemotherapy, radiotherapy, or antibody therapy.
30) The method of embodiments 1-29, wherein the subject is a human.
31) A composition comprising:
    (a) an oncolytic adenovirus; and
    (b) an anti-PD-1 antibody.
32) The composition of embodiment 31, wherein the oncolytic adenovirus is an adenovirus serotype 5 strain, and/or wherein the oncolytic adenovirus is selectively replication competent in cells defective in the Rb/p16 tumor suppressor pathway, and/or wherein the oncolytic adenovirus comprises a deletion of the 24 nucleotides encoding amino acids 122 to 129 of the adenoviral E1A protein, and/or wherein the oncolytic adenovirus comprises an integrin binding RGD-4C motif.
33) The composition of embodiments 31-32, wherein the oncolytic adenovirus is DNX-2401.
34) The composition of embodiments 31-33, wherein the anti-PD1 antibody is a humanized antibody.
35) The composition of embodiments 31-34, wherein the anti-PD1 antibody is pembrolizumab.
36) The composition of embodiments 31-35, wherein the composition is formulated for intratumoral delivery.
37) The composition of embodiments 31-35, wherein the composition is formulated for intravenous infusion.
38) The composition of embodiments 31-37, wherein the oncolytic adenovirus is comprised in a unit dose of $5\times10^8$ viral particles per dose, $5\times10^9$ viral particles per dose, or $5\times10^{10}$ viral particles per dose.
39) The composition of embodiments 31-38, wherein the anti-PD1 antibody is comprised in a unit dose of 200 mg.
40) The composition of embodiments 31-39, further comprising one or more of a steroid, an anticonvulsant or an antibody that inhibits vascular endothelial growth factor A.
41) A composition comprising an oncolytic adenovirus of adenovirus serotype 5 strain, wherein the oncolytic adenovirus is selectively replication competent in cells defective in the Rb/p16 tumor suppressor pathway, wherein the oncolytic adenovirus comprises a deletion of the 24 nucleotides encoding amino acids 122 to 129 of the adenoviral E1A protein, and wherein the oncolytic adenovirus comprises an integrin binding RGD-4C motif.
42) The composition of embodiment 41, wherein the oncolytic adenovirus is DNX-2401.
43) The composition of embodiments 41-42, wherein the oncolytic adenovirus is comprised in a unit dose of $5\times10^8$ viral particles per dose.
44) The composition of embodiments 41-42, wherein the oncolytic adenovirus is comprised in a unit dose of $5\times10^9$ viral particles per dose.
45) The composition of embodiments 41-42, wherein the oncolytic adenovirus is comprised in a unit dose of $5\times10^{10}$ viral particles per dose.

Any of the various embodiments described above can be combined to provide further embodiments. All of the U.S. patents, U.S. patent application publications, U.S. patent applications, PCT application publications, foreign patents, foreign patent applications and non-patent publications referred to in this specification, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

VII. REFERENCES

The following references, to the extent that they provide exemplary procedural or other details supplementary to those set forth herein, are specifically incorporated herein by reference.

U.S. Pat. No. 8,992,458
U.S. Patent Publication 2013/0035660
U.S. Patent Publication 2013/0035574
U.S. Patent Publication 2013/0035560
I. Mei, Z., et al., Tumour-infiltrating inflammation and prognosis in colorectal cancer: systematic review and meta-analysis. Br J Cancer, 2014. 110(6): p. 1595-605.
II. Salgado, R., et al., Harmonization of the evaluation of tumor infiltrating lymphocytes (TILs) in breast cancer: recommendations by an international TILs-working group 2014. Ann Oncol, 2014
III. Schatton, T., et al., Tumor-infiltrating lymphocytes and their significance in melanoma prognosis. Methods Mol Biol, 2014. 1102: p. 287-324.
IV. Gooden, M. J., et al., The prognostic influence of tumour-infiltrating lymphocytes in cancer: a systematic review with meta-analysis. Br J Cancer, 2011. 105(1): p. 93-103.
V. Schreiber, R. D., L. J. Old, and M. J. Smyth, Cancer immunoediting: integrating immunity's roles in cancer suppression and promotion. Science, 2011. 331(6024): p. 1565-70.
VI. Bremnes, R. M., et al., The role of tumor-infiltrating immune cells and chronic inflammation at the tumor site on cancer development, progression, and prognosis: emphasis on non-small cell lung cancer. J Thorac Oncol, 2011. 6(4): p. 824-33.
VII. Talmadge, J. E., Immune cell infiltration of primary and metastatic lesions: mechanisms and clinical impact. Semin Cancer Biol, 2011. 21(2): p. 131-8.

VIII. Shirabe, K., et al., Tumor-infiltrating lymphocytes and hepatocellular carcinoma: pathology and clinical management. Int J Clin Oncol, 2010. 15(6): p. 552-8.

IX. Nosho, K., et al., Tumour-infiltrating T-cell subsets, molecular changes in colorectal cancer, and prognosis: cohort study and literature review. J Pathol, 2010. 222(4): p. 350-66.

X. Bellati, F., et al., Immunology of gynecologic neoplasms: analysis of the prognostic significance of the immune status. Curr Cancer Drug Targets, 2009. 9(4): p. 541-65.

XI. Oble, D. A., et al., Focus on TILs: prognostic significance of tumor infiltrating lymphocytes in human melanoma. Cancer Immun, 2009. 9: p. 3.

XII. Uppaluri, R., G. P. Dunn, and J. S. Lewis, Jr., Focus on TILs: prognostic significance of tumor infiltrating lymphocytes in head and neck cancers. Cancer Immun, 2008. 8: p. 16.

XIII. Dunn, G. P., I. F. Dunn, and W. T. Curry, Focus on TILs: Prognostic significance of tumor infiltrating lymphocytes in human glioma. Cancer Immun, 2007. 7: p. 12.

XIV. Chang, W. J., et al., Inflammation-related factors predicting prognosis of gastric cancer. World J Gastroenterol, 2014. 20(16): p. 4586-96.

XV. Alonso M M, Gomez-Manzano C, Bekele B N, Yung W K, Fueyo J. Adenovirus-based strategies overcome temozolomide resistance by silencing the 06-methylguanine-DNA methyltransferase promoter. Cancer research 2007; 67:11499-504.

XVI. Alonso M M, Jiang H, Yokoyama T, et al. Delta-24-RGD in combination with RAD001 induces enhanced anti-glioma effect viac autophagic cell death. Molecular therapy: the journal of the American Society of Gene Therapy 2008; 16:487-93.

XVII. Fueyo J, Alemany R, Gomez-Manzano C, et al. Preclinical characterization of the antiglioma activity of a tropism-enhanced adenovirus targeted to the retinoblastoma pathway. Journal of the National Cancer Institute 2003; 95:652-60.

XVIII. Fueyo J, Gomez-Manzano C, Alemany R, et al. A mutant oncolytic adenovirus targeting the Rb pathway produces anti-glioma effect in vivo. Oncogene 2000; 19:2-12.

XIX. Fueyo J, Gomez-Manzano C, Yung W K. Advances in translational research in neuro-oncology. Archives of neurology 2011; 68:303-8.

XX. Wang M, Hemminki A, Siegal G P, et al. Adenoviruses with an RGD-4C modification of the fiber knob elicit a neutralizing antibody response but continue to allow enhanced gene delivery. Gynecologic oncology 2005; 96:341-8.

XXI. Wolchok J D, Hoos A, O'Day S, et al. Guidelines for the evaluation of immune therapy activity in solid tumors: immune-related response criteria. Clin Cancer Res. 2009; 15(23):7412-7420.

XXII. Gomez-Manzano C, Fueyo J. Oncolytic adenoviruses for the treatment of brain tumors. Current opinion in molecular therapeutics 2010; 12:530-7.

XXIII. Jiang H, Conrad C, Fueyo J, Gomez-Manzano C, Liu T J. Oncolytic adenoviruses for malignant glioma therapy. Frontiers in bioscience: a journal and virtual library 2003; 8:d577-88.

XXIV. Bilbao G, Contreras J L, Dmitriev I, et al. Genetically modified adenovirus vector containing an RGD peptide in the HI loop of the fiber knob improves gene transfer to nonhuman primate isolated pancreatic islets. American journal of transplantation: official journal of the American Society of Transplantation and the American Society of Transplant Surgeons 2002; 2:237-43.

XXV. Poole, R. M., Pembrolizumab: First Global Approval. Drugs, 2014.

XXVI. Disis, M. L., Immune regulation of cancer. J Clin Oncol, 2010. 28(29): p. 4531-8.

XXVII. Preston, C. C., et al., The ratios of CD8+ T cells to CD4+CD25+ FOXP3+ and FOXP3− T cells correlate with poor clinical outcome in human serous ovarian cancer. PLoS One, 2013. 8(11): p. e80063.

XXVII. Yoon, H. H., et al., Prognostic impact of FoxP3+ regulatory T cells in relation to CD8+T lymphocyte density in human colon carcinomas. PLoS One, 2012. 7(8): p. e42274.

XXIX. Kim, S. T., et al., Tumor-infiltrating lymphocytes, tumor characteristics, and recurrence in patients with early breast cancer. Am J Clin Oncol, 2013. 36(3): p. 224-31.

XXX. Mathai, A. M., et al., Role of Foxp3-positive tumor-infiltrating lymphocytes in the histologic features and clinical outcomes of hepatocellular carcinoma. Am J Surg Pathol, 2012. 36(7): p. 980-6.

XXXI. Liu, F., et al., CD8(+) cytotoxic T cell and FOXP3(+) regulatory T cell infiltration in relation to breast cancer survival and molecular subtypes. Breast Cancer Res Treat, 2011. 130(2): p. 645-55.

XXXI. Kirk, R., Risk factors. CD8+:FOXP3+ cell ratio is a novel survival marker for colorectal cancer. Nat Rev Clin Oncol, 2010. 7(6): p. 299.

XXXII. Pedoeem, A., et al., Programmed death-1 pathway in cancer and autoimmunity. Clin Immunol, 2014. 153(1): p. 145-52.

XXXIV. Zhang, X., et al., Structural and functional analysis of the costimulatory receptor programmed death-1. Immunity, 2004. 20(3): p. 337-47.

XXXV. Lazar-Molnar, E., et al., Crystal structure of the complex between programmed death-1 (PD-1) and its ligand PD-L2. Proc Natl Acad Sci USA, 2008. 105(30): p. 10483-8.

XXXVI. Lin, D. Y., et al., The PD-1/PD-L1 complex resembles the antigen-binding Fv domains of antibodies and T cell receptors. Proc Natl Acad Sci USA, 2008. 105(8): p. 3011-6.

XXXVII. Cheng, X., et al., Structure and interactions of the human programmed cell death 1 receptor. J Biol Chem, 2013. 288(17): p. 11771-85.

XXXVIII. Sheppard, K. A., et al., PD-1 inhibits T-cell receptor induced phosphorylation of the ZAP70/CD3zeta signalosome and downstream signaling to PKCtheta. FEBS Lett, 2004. 574(1-3): p. 37-41.

XXXIX. Ott, P. A., F. S. Hodi, and C. Robert, CTLA-4 and PD-1/PD-L1 blockade: new immunotherapeutic modalities with durable clinical benefit in melanoma patients. Clin Cancer Res, 2013. 19(19): p. 5300-9.

XL. Yao, S. and L. Chen, PD-1 as an immune modulatory receptor. Cancer J, 2014. 20(4): p. 26

XLI. Nishimura, H., et al., Developmentally regulated expression of the PD-1 protein on the surface of double-negative (CD4-CD8-) thymocytes. Int Immunol, 1996. 8(5): p. 773-80.

XLII. Huang, X., et al., PD-1 expression by macrophages plays a pathologic role in altering microbial clearance and the innate inflammatory response to sepsis. Proc Natl Acad Sci USA, 2009. 106(15): p. 6303-8.

XLIII. Pena-Cruz, V., et al., PD-1 on immature and PD-1 ligands on migratory human Langerhans cells regulate antigen-presenting cell activity. J Invest Dermatol, 2010. 130(9): p. 2222-30.

XLIV. Keir, M. E., et al., PD-1 and its ligands in tolerance and immunity. Annu Rev Immunol, 2008. 26: p. 677-704.

XLV. Karim, R., et al., Tumor-expressed B7-H1 and B7-DC in relation to PD-1+ T-cell infiltration and survival of patients with cervical carcinoma. Clin Cancer Res, 2009. 15(20): p. 6341-7.

XLVI. Taube, J. M., et al., Colocalization of inflammatory response with B7-h1 expression in human melanocytic lesions supports an adaptive resistance mechanism of immune escape. Sci Transl Med, 2012. 4(127): p. 127ra37.

XLVII. Sanmamed, M. F. and L. Chen, Inducible expression of B7-H1 (PD-L1) and its selective role in tumor site immune modulation. Cancer J, 2014. 20(4): p. 256-61.

XLVIII. Topalian, S. L., C. G. Drake, and D. M. Pardoll, Targeting the PD-1/B7-H1(PD-L1) pathway to activate anti-tumor immunity. Curr Opin Immunol, 2012. 24(2): p. 207-12.

XLIX. Hirano, F., et al., Blockade of B7-H1 and PD-1 by monoclonal antibodies potentiates cancer therapeutic immunity. Cancer Res, 2005. 65(3): p. 1089-96.

L. Blank, C., et al., PD-L1/B7H-1 inhibits the effector phase of tumor rejection by T cell receptor (TCR) transgenic CD8+ T cells. Cancer Res, 2004. 64(3): p. 1140-5.

LI. Weber, J., Immune checkpoint proteins: a new therapeutic paradigm for cancer—preclinical background: CTLA-4 and PD-1 blockade. Semin Oncol, 2010. 37(5): p. 430-9.

LII. Strome, S. E., et al., B7-H1 blockade augments adoptive T-cell immunotherapy for squamous cell carcinoma. Cancer Res, 2003. 63(19): p. 6501-5.

LIII. Spranger, S., et al., Mechanism of tumor rejection with doublets of CTLA-4, PD-1/PD-L1, or IDO blockade involves restored IL-2 production and proliferation of CD8(+) T cells directly within the tumor microenvironment. J Immunother Cancer, 2014. 2: p. 3.

LIV. Curran, M. A., et al., PD-1 and CTLA-4 combination blockade expands infiltrating T cells and reduces regulatory T and myeloid cells within B16 melanoma tumors. Proc Natl Acad Sci USA, 2010. 107(9): p. 4275-80.

LV. Pilon-Thomas, S., et al., Blockade of programmed death ligand 1 enhances the therapeutic efficacy of combination immunotherapy against melanoma. J Immunol, 2010. 184(7): p. 3442-9.

LVI. Nomi, T., et al., Clinical significance and therapeutic potential of the programmed death-1 ligand/programmed death-1 pathway in human pancreatic cancer. Clin Cancer Res, 2007. 13(7): p. 2151-7.

LVII. Wick W, et al. Phase III Study of Enzastaurin Compared With Lomustine in the Treatment of Recurrent Intracranial Glioblastoma. J Clin Oncol 2010; 28:1168-1174.

LVIII. Lamborn K R, Yung W K A, Chang S M, et al. Progression-free survival: an important end point in evaluating therapy for recurrent high-grade gliomas. Neuro-Oncology. 2008; 10(2): 162-170.

The invention claimed is:

1. A method of treating a subject having brain tumor comprising:
   (a) administering an oncolytic adenovirus to said subject;
   (b) administering an anti-PD-1 antibody to said subject; and
   (c) assessing tumor response by measuring tumor size;
   wherein the oncolytic adenovirus is an adenovirus serotype 5 strain, is selectively replication competent in cells defective in the Rb/p16 tumor suppressor pathway, contains a deletion of the 24 nucleotides encoding amino acids 122 to 129 of the adenoviral E1A protein, and/or contains an integrin binding RGD-4C motif; and
   wherein the anti-PD-1 antibody is pembrolizumab administered at 200 mg per dose; and
   wherein the tumor exhibits reduced growth, no growth, a 10% reduction in tumor mass, a 20% reduction in tumor mass, a 30% reduction in tumor mass, a 40% reduction in tumor mass, a 50% reduction in tumor mass, a 60% reduction in tumor mass, a 70% reduction in tumor mass, an 80% reduction in tumor mass, a 90% reduction in tumor mass, or a 100% reduction in tumor mass following initiation of treatment.

2. The method of claim 1, wherein the oncolytic adenovirus is DNX-2401.

3. The method of claim 1, wherein the oncolytic adenovirus is delivered intratumorally.

4. The method of claim 3, wherein the oncolytic adenovirus is delivered via cannula or needle.

5. The method of claim 1, wherein the oncolytic adenovirus is delivered at $5 \times 10^8$ viral particles per dose, $5 \times 10^9$ viral particles per dose, or $5 \times 10^{10}$ viral particles per dose.

6. The method of claim 1, wherein the anti-PD1 antibody is delivered by intravenous infusion.

7. The method of claim 1, wherein the anti-PD1 antibody dose is administered over 30 minutes.

8. The method of claim 1, wherein a single dose of the oncolytic adenovirus is provided prior to three consecutive doses of the anti-PD1 antibody.

9. The method of claim 8, wherein the time between oncolytic adenovirus administration and the first administration of the anti-PD1 antibody is about 7-9 days.

10. The method of claim 8, wherein the time between sequential administrations of the anti-PD1 antibody is about three weeks.

11. The method of claim 1, further comprising administering to the subject one or more of a steroid, an anticonvulsant or an antibody that inhibits vascular endothelial growth factor A.

12. The method of claim 8, wherein treating further comprises additional administrations of the anti-PD1 antibody for up to 105 weeks or 24 months from the date of oncolytic adenovirus administration.

13. The method of claim 1, wherein said subject is further evaluated for one of more of overall survival, clinical benefit rate, Karnofsky performance status, neurologic status, cytokine levels, lymphocyte levels, or a biomarker.

14. The method of claim 13, wherein said biomarker is PD-1 level or PDL-1 level.

15. The method of claim 1, wherein tumor size is measured by MRI.

16. The method of claim 1, further comprising stereotactically-guided biopsy of the brain tumor.

17. The method of claim 1, wherein the brain tumor is glioblastoma multiforme.

18. The method of claim 1, wherein the brain tumor is gliosarcoma.

19. The method of claim 1, wherein the subject exhibits an overall survival of at least 9 months, 12 months, 15 months, 18 months, 24 months, 36 months or 48 months, any interval therebetween.

20. The method of claim 1, wherein the subject exhibits an increase in overall survival, as compared to an untreated control subject, of at least 6 months, 9 months, 12 months, 15 months, 18 months, 24 months, 36 months or 48 months, any interval therebetween.

21. The method of claim 1, wherein the tumor exhibits reduced growth or no growth following initiation of treatment.

22. The method of claim 1, wherein the Karnofsky performance status improves or remains unchanged following step (b).

23. The method of claim 1, wherein there is a statistically measurable clinical benefit.

24. The method of claim 1, wherein the subject exhibits recurrent or progressive brain tumor following previous treatment.

25. The method of claim 1, wherein the previous treatment was chemotherapy, radiotherapy, or antibody therapy.

26. The method of claim 1, wherein the subject is a human.

27. The method of claim 1, wherein the tumor exhibits a 10% reduction in tumor mass, a 20% reduction in tumor mass, a 30% reduction in tumor mass, a 40% reduction in tumor mass, a 50% reduction in tumor mass, a 60% reduction in tumor mass, a 70% reduction in tumor mass, an 80% reduction in tumor mass, a 90% reduction in tumor mass, or a 100% reduction in tumor mass following initiation of treatment.

28. The method of claim 1, wherein the tumor exhibits a 10% reduction in tumor mass following initiation of treatment.

29. The method of claim 1, wherein the tumor exhibits a 20% reduction in tumor mass following initiation of treatment.

30. The method of claim 1, wherein the tumor exhibits a 50% reduction in tumor mass following initiation of treatment.

31. The method of claim 1, wherein the tumor exhibits a 50%, 60%, 70%, 80% or 90% reduction in tumor mass following initiation of treatment.

* * * * *